US008088370B2

(12) United States Patent
Pecora et al.

(10) Patent No.: US 8,088,370 B2
(45) Date of Patent: *Jan. 3, 2012

(54) COMPOSITIONS AND METHODS OF VASCULAR INJURY REPAIR

(75) Inventors: Andrew Pecora, Ridgewood, NJ (US); Robert Preti, Ridgefield, CT (US)

(73) Assignee: Amorcyte, Inc., Hackensack, NJ (US)

( * ) Notice: Subject to any disclaimer, the term of this patent is extended or adjusted under 35 U.S.C. 154(b) by 427 days.

This patent is subject to a terminal disclaimer.

(21) Appl. No.: 12/401,291

(22) Filed: Mar. 10, 2009

(65) Prior Publication Data

US 2009/0226402 A1 Sep. 10, 2009

Related U.S. Application Data

(62) Division of application No. 11/552,396, filed on Oct. 24, 2006, now Pat. No. 7,794,705.

(60) Provisional application No. 60/734,151, filed on Nov. 7, 2005.

(51) Int. Cl.
*A61K 35/12* (2006.01)

(52) U.S. Cl. ........ 424/93.7; 424/577; 424/531; 435/372

(58) Field of Classification Search ........................ None
See application file for complete search history.

(56) References Cited

U.S. PATENT DOCUMENTS

| | | | |
|---|---|---|---|
| 5,750,397 | A | 5/1998 | Tsukamoto et al. |
| 5,980,887 | A | 11/1999 | Isner et al. |
| 6,287,265 | B1 | 9/2001 | Gleason |
| 6,569,428 | B1 | 5/2003 | Isner et al. |
| 6,569,434 | B1 | 5/2003 | Bayne et al. |
| 6,676,937 | B1 | 1/2004 | Isner et al. |
| 6,933,134 | B2 | 8/2005 | Bayne et al. |
| 7,135,171 | B2 | 11/2006 | Edelberg et al. |
| 7,172,758 | B2 | 2/2007 | Colb et al. |
| 2002/0061587 | A1 | 5/2002 | Anversa |
| 2002/0098167 | A1 | 7/2002 | Anversa et al. |
| 2002/0142457 | A1 | 10/2002 | Umezawa et al. |
| 2002/0172663 | A1 | 11/2002 | Palasis |
| 2003/0054973 | A1 | 3/2003 | Anversa |
| 2003/0059414 | A1 | 3/2003 | Ho et al. |
| 2003/0113304 | A1 | 6/2003 | Burkhoff |
| 2003/0148512 | A1 | 8/2003 | Fanslow, III et al. |
| 2003/0199464 | A1 | 10/2003 | Itescu |
| 2003/0232050 | A1 | 12/2003 | Isner et al. |
| 2004/0058412 | A1 | 3/2004 | Ho et al. |
| 2004/0067218 | A1 | 4/2004 | Casteilla et al. |
| 2004/0076619 | A1 | 4/2004 | Anversa et al. |
| 2004/0131585 | A1 | 7/2004 | Itescu |
| 2004/0136966 | A1 | 7/2004 | Anversa et al. |
| 2004/0136973 | A1 | 7/2004 | Huberman et al. |
| 2004/0197310 | A1 | 10/2004 | Sanberg et al. |
| 2004/0219136 | A1 | 11/2004 | Hariri |
| 2004/0247564 | A1 | 12/2004 | Itescu |
| 2004/0258670 | A1 | 12/2004 | Laughlin et al. |
| 2005/0069527 | A1 | 3/2005 | Laughlin et al. |
| 2005/0095228 | A1 | 5/2005 | Fraser et al. |
| 2005/0129663 | A1 | 6/2005 | Fulga et al. |
| 2005/0232905 | A1 | 10/2005 | Yeh |
| 2005/0233992 | A1 | 10/2005 | Itescu |
| 2006/0008450 | A1 | 1/2006 | Verfaillie et al. |
| 2006/0193836 | A1 | 8/2006 | Rudd |
| 2006/0239983 | A1 | 10/2006 | Anversa |
| 2007/0059288 | A1 | 3/2007 | Dinsmore et al. |
| 2007/0065417 | A1 | 3/2007 | Chancellor et al. |
| 2007/0077201 | A1 | 4/2007 | Reading et al. |

FOREIGN PATENT DOCUMENTS

| | | |
|---|---|---|
| JP | 2006115771 | 5/2006 |
| WO | 9325216 | 12/1993 |
| WO | 9505843 | 3/1995 |
| WO | 9819712 | 5/1998 |
| WO | 9937751 | 7/1999 |
| WO | 9961584 | 12/1999 |
| WO | 0006704 | 2/2000 |
| WO | 0012683 | 3/2000 |
| WO | 0132842 | 5/2001 |
| WO | 0171016 | 9/2001 |
| WO | 0209650 | 2/2002 |
| WO | 0213760 | 2/2002 |
| WO | 0220003 | 3/2002 |
| WO | 0228355 | 4/2002 |
| WO | 02064157 | 8/2002 |
| WO | 02081007 | 10/2002 |
| WO | 02097066 | 12/2002 |
| WO | 03060077 | 7/2003 |
| WO | 03025149 | 12/2003 |
| WO | 03103611 | 12/2003 |
| WO | 2004007697 | 1/2004 |
| WO | 2004010959 | 2/2004 |
| WO | 2004019767 | 3/2004 |
| WO | 2005083061 | 9/2005 |
| WO | 2006093860 | 9/2006 |

OTHER PUBLICATIONS

Asahara, T. et al., "VEGF contributes to postnatal neovascularization by mobilizing bone marrow-derived endothelial progenitor cells", The EMBO Journal, Jul. 15, 1999, vol. 18, No. 14, pp. 3964-3972.

Shi, Q. et al., "Evidence for circulating bone marrow-derived endothelial cells", Blood, Jul. 15, 1998, vol. 92, No. 2, pp. 362-367.

Hill, J. M. et al., "Circulating endothelial progenitor cells, vascular function, and cardiovascular risk", New England Journal of Medicine, Feb. 13, 2003, vol. 348, No. 7, pp. 593-600.

(Continued)

*Primary Examiner* — Allison Ford

(74) *Attorney, Agent, or Firm* — Beverly W. Lubit; Greenberg Traurig, LLP

(57) ABSTRACT

The present invention relates to pharmaceutical compositions comprising a chemotactic hematopoietic stem cell product comprising an enriched population of CD34+ cells containing a subpopulation of cells having chemotactic activity, methods of preparing these compositions and use of these compositions to treat or repair vascular injury, including infarcted myocardium.

23 Claims, 3 Drawing Sheets

OTHER PUBLICATIONS

Vasa, M. et al., "Number and migratory activity of circulating endothelial progenitor cells inversely correlate with risk factors for coronary artery disease", Circulation Research, Jul. 6, 2001, vol. 89, No. 1, pp. E1-E7.

Asahara, T. et al., "Isolation of putative progenitor endothelial cells for angiogenesis", Science, Feb. 14, 1997, vol. 275, No. 5302, pp. 964-967.

Lin, Y. et al., "Origins of circulating endothelial cells and endothelial outgrowth from blood", Journal of Clinical Investigation, Jan. 2000, vol. 105, No. 1, pp. 71-77.

Camargo, F. D. et al., "Single hematopoietic stem cells generate skeletal muscle through myeloid intermediates", Nature Medicine, Dec. 2003, vol. 9, No. 12, pp. 1520-1527.

Takahashi, T. et al., "Ischemia- and cytokine-induced mobilization of bone marrow-derived endothelial progenitor cells for neovascularization", Nature Medicine, Apr. 1999, vol. 5, No. 4, pp. 434-438.

Ceradini, D. J. et al., "Progenitor cell trafficking is regulated by hypoxic gradients through HIF-1 induction of SDF-1", Nature Medicine, Aug. 2004, vol. 10, No. 8, pp. 858-864.

Askari, A. T. et al., "Effect of stromal-cell-derived factor 1 on stem-cell homing and tissue regeneration in ischaemic cardiomyopathy", The Lancet, Aug. 30, 2003, vol. 362, No. 9385, pp. 697-703.

Yamaguchi, J. et al., "Stromal cell-derived factor-1 effects on ex vivo expanded endothelial progenitor cell recruitment for ischemic neovascularization", Circulation, Mar. 11, 2003, vol. 107, No. 9, pp. 1322-1328.

Peichev, M. et al., "Expression of VEGFR-2 and AC133 by circulating human CD34(+) cells identifies a population of functional endothelial precursors", Blood, Feb. 1, 2000, vol. 95, No. 3, pp. 952-958.

Orlic, D. et al., "Bone marrow cells regenerate infarcted myocardium", Nature, Apr. 5, 2001, vol. 410, No. 6829, pp. 701-705.

Kocher, A. A. et al., "Neovascularization of ischemic myocardium by human bone-marrow-derived angioblasts prevents cardiomyocyte apoptosis, reduces remodeling and improves cardiac function", Nature Medicine, Apr. 2001, vol. 7, No. 4, pp. 430-436.

Orlic, D., "Cytokine mobilized CD34+ cells do not benefit Rhesus monkeys following induced myocardial infarction", Blood suppl., 2002, vol. 100, Abstract #94.

Etzion, S. et al., "Influence of embryonic cardiomyocyte transplantation on the progression of heart failure in a rat model of extensive myocardial infarction", Journal of Molecular and Cellular Cardiology, Jul. 2001, vol. 33, No. 7, pp. 1321-1330.

Soonpaa, M. H. et al., "Formation of nascent intercalated disks between grafted fetal cardiomyocytes and host myocardium", Science, Apr. 1, 1994, vol. 264, No. 5155, pp. 98-101.

Ruhparwar, A. et al., "Transplanted fetal cardiomyocytes as cardiac pacemaker", European Journal of Cardio-thoracic Surgery, May 2002, vol. 21, No. 5, pp. 853-857.

Li, R. K. et al., "Smooth muscle cell transplantation into myocardial scar tissue improves heart function", Journal of Molecular and Cellular Cardiology, Mar. 1999, vol. 31, No. 3, pp. 513-522.

Koh, J. Y. et al., "Long-term survival of AT-1 cardiomyocyte grafts in syngeneic myocardium", The American Journal of Physiology, May 1993, vol. 264, No. 5 (Pt. 2), pp. H1727-H1733.

Robinson, S. W. et al., "Arterial delivery of genetically labelled skeletal myoblasts to the murine heart: long-term survival and phenotypic modification of implanted myoblasts", Cell Transplantation, 1996, vol. 5, No. 1, pp. 77-91.

Dorfman, J. et al., "Myocardial tissue engineering with autologous myoblast implantation", The Journal of Thoracic and Cardiovascular Surgery, Nov. 1998, vol. 116, No. 5, pp. 744-751.

Pouzet, B. et al., "Factors affecting functional outcome after autologous skeletal myoblast transplantation", The Annals of Thoracic Surgery, Mar. 2001, vol. 71, No. 3, pp. 844-851.

Murry, C. E. et al., "Skeletal myoblast transplantation for repair of myocardial necrosis", The Journal of Clinical Investigation, Dec. 1, 1996, vol. 98, No. 11, pp. 2512-2523.

Jain, M. et al., "Cell therapy attenuates deleterious ventricular remodeling and improves cardiac performance after myocardial infarction", Circulation, Apr. 10, 2001, vol. 103, No. 14, pp. 1920-1927.

Atkins, B. Z. et al., "Cellular cardiomyoplasty improves diastolic properties of injured heart", The Journal of Surgical Research, Aug. 1999, vol. 85, No. 2, pp. 234-242.

Atkins, B. Z. et al., "Myogenic cell transplantation improves in vivo regional performance in infarcted rabbit myocardium", The Journal of Heart and Lung Transplantation, Dec. 1999, vol. 18, No. 12, pp. 1173-1180.

Taylor, D. A. et al., "Regenerating functional myocardium: improved performance after skeletal myoblast transplantation", Nature Medicine, Aug. 1998, vol. 4, No. 8, pp. 929-933.

Li, R. K. et al., "Autologous porcine heart cell transplantation improved heart function after a myocardial infarction", The Journal of Thoracic and Cardiovascular Surgery, Jan. 2000, vol. 119, No. 1, pp. 62-68.

Watanabe, E. et al., "Cardiomyocyte transplantation in a porcine myocardial infarction model", Cell Transplantation, 1998, vol. 7, No. 3, pp. 239-246.

Marelli, D. et al., "Cell transplantation for myocardial repair: an experimental approach", Cell Transplantation, 1992, vol. 1, No. 6, pp. 383-390.

Chiu, R. C. et al., "Cellular cardiomyoplasty: myocardial regeneration with satellite cell implantation", The Annals of Thoracic Surgery, Jul. 1995, vol. 60, No. 1, pp. 12-18.

Rajnoch, C. et al., "Cellular therapy reverses myocardial dysfunction", The Journal of Thoracic Cardiovascular Surgery, May 2001, vol. 121, No. 5, pp. 871-878.

Toma, C. et al., "Human mesenchymal stem cells differentiate to a cardiomyocyte phenotype in the adult murine heart", Circulation, Jan. 1, 2002, vol. 105, No. 1. pp. 93-98.

Shake, J. G. et al., "Mesenchymal stem cell implantation in a swine myocardial infarct model: engraftment and functional effects", The Annals of Thoracic Surgery, Jun. 2002, vol. 73, No. 6, pp. 1919-1926.

Mangi, A. A. et al., Mesenchymal stem cells modified with Akt prevent remodeling and restore performance of infarcted hearts, Nature Medicine, Sep. 2003, vol. 9, No. 9, pp. 1195-1201.

Wakitani, S. et al., "Myogenic cells derived from rat bone marrow mesenchymal stem cells exposed to 5-azacytidine", Muscle & Nerve, Dec. 1995, vol. 18, No. 12, pp. 1417-1426.

Korbling, M. et al., "Hepatocytes and epithelial cells of donor origin in recipients of peripheral-blood stem cells", The New England Journal of Medicine, Mar. 7, 2002, vol. 346, No. 10, pp. 738-746.

Jiang, Y. et al., "Multipotent progenitor cells can be isolated from postnatal murine bone marrow, muscle, and brain", Experimental Hematology, Aug. 2002, vol. 30, No. 8, pp. 896-904.

Krause, D. S. et al., "Multi-organ, multi-lineage engraftment by a single bone marrow-derived stem cell", Cell, May 4, 2001, vol. 105, No. 3, pp. 369-377.

Krause, D. S., "Plasticity of marrow-derived stem cells", Gene Therapy, Jun. 2002, vol. 9, No. 11, pp. 754-758.

Okamoto, R. et al., "Damaged epithelia regenerated by bone marrow-derived cells in the human gastrointestinal tract", Nature Medicine, Sep. 2002, vol. 8, No. 9, pp. 1011-1017.

Labarge, M. A. et al., "Biological progression from adult bone marrow to mononucleate muscle stem cell to multinucleate muscle fiber in response to injury", Cell, Nov. 15, 2002, vol. 111, No. 4, pp. 589-601.

Balsam, L. B. et al., "Haematopoietic stem cells adopt mature haematopoietic fates in ischaemic myocardium", Nature, Apr. 8, 2004, vol. 428, No. 6983, pp. 668-673.

Ziegelhoeffer, T. et al., "Bone marrow-derived cells do not incorporate into the adult growing vasculature", Circulation Research, Feb. 6, 2004, vol. 94, No. 2, pp. 230-238.

Strauer, B. E. et al., "Repair of infarcted myocardium by autologous intracoronary mononuclear bone marrow cell transplantation in humans", Circulation, Oct. 8, 2002, vol. 106, No. 15, pp. 1913-1918.

Penn, M. S. et al., "Autologous cell transplantation for the treatment of damaged myocardium", Progress in Cardiovascular Diseases, Jul.-Aug. 2002, vol. 45, No. 1, pp. 21-32.

Kawamoto, A. et al., "Therapeutic potential of ex vivo expanded endothelial progenitor cells for myocardial ischemia", Circulation, Feb. 6, 2001, vol. 103, No. 5, pp. 634-637.

Wang, J. S. et al., "The coronary delivery of marrow stromal cells for myocardial regeneration: pathophysiologic and therapeutic implications", The Journal of Thoracic and Cardiovascular Surgery, Oct. 2001, vol. 122, No. 4, pp. 699-705.

Tomita, S. et al., "Autologous transplantation of bone marrow cells improves damaged heart function", Circulation, Nov. 9, 1999, vol. 100 (19 Suppl.), pp. II247-II256.

Kawamoto et al., "CD34-Positive Cells Exhibit Increased Potency and Safety for Therapeutic Neovascularization After Myocardial Infarction Compared With Total Mononuclear Cells", Circulation, 2006, vol. 114, pp. 2163-2169.

Szilvassy et al., "Organ-Selective Homing Defines Engraftment Kinetics of Murine Hematopoietic Stem Cells and Is Compromised by Ex Vivo Expansion", Blood, 1999, vol. 93, pp. 1557-1566.

Jo, D.-Y. et al., "Chemotaxis of primitive hematopoietic cells in response to stromal cell-derived factor-1", Journal of Clinical Investigation, Jan. 2000, vol. 105, No. 1, pp. 101-111.

Hill, J. M. et al., "Circulating Endothelial Progenitor Cells, Vascular Function, and Cardiovascular Risk", The New England Journal of Medicine, Feb. 13, 2003, vol. 348, pp. 593-600.

Vasa, M. et al., "Number and Migratory Activity of Circulating Endothelial Progenitor Cells Inversely Correlate with Risk Factors for Coronary Artery Disease", Division of Molecular Cardiology, Department of Internal Medicine IV and Department of Hematology, Internal Medicine III, University of Frankfurt, Germany, Apr. 23, 2001, pp. 1-7.

Chen, H. K. et al., "Combined cord blood stem cells and gene therapy enhances angiogenesis and improves cardiac performance in mouse after acute myocardial infarction", European Journal of Clinical Investigation, Nov. 2005, vol. 35, No. 11, 677-686.

Hayashi, M. et al., "Comparison of intramyocardial and intravenous routes of delivering bone marrow cells for the treatment of ischemic heart disease: an experimental study", Cell Transplantation, 2004, vol. 13, No. 6, 639-647.

Hirata, Y. et al., "Human umbilical cord blood cells improve cardiac function after myocardial infarction", Biochemical and Biophysical Research Communications, Feb. 11, 2005, vol. 327, No. 2, pp. 609-614.

Hofmann, M. et al., "Monitoring of Bone Marrow Cell Homing Into the Infarcted Human Myocardium", Circulation, 2005, vol. 111, pp. 2198-2202.

Ince, H. et al., "Prevention of Left Ventricular Remodeling With Granulocyte Colony-Stimulating Factor After Acute Myocardial Infarction: Final 1-year Results of the Front-Integrated Revascularization and Stem Cell Liberation in Evolving Acute Myocardial Infarction by Granulocyte Colony-Stimulating Factor (Firstline-AMI) Trial", Circulation, Aug. 30, 2005, vol. 112 (9 Suppl.), pp. I-73-I-80.

Jackson, K. A. et al., "Regeneration of ischemic cardiac muscle and vascular endothelium by adult stem cells", The Journal of Clinical Investigation, 2001, vol. 107, No. 11, pp. 1395-1402.

Kim, Y.-H. et al., "Intramyocardial transplantation of circulating CD34+ cells: source of stem cells for myocardial regeneration", Journal of Korean Medical Science, Dec. 2003, vol. 18, No. 6, pp. 797-803.

Leone, A. M. et al., "Mobilization of bone marrow-derived stem cells after myocardial infarction and left ventricular function", European Heart Journal, Jun. 2005, vol. 26, No. 12, pp. 1196-1204.

Ma, N. et al., "Human cord blood cells induce angiogenesis following myocardial infarction in NOD/scid-mice", Cardiovascular Research, Apr. 1, 2005, vol. 66, No. 1, pp. 45-54.

Muller-Ehmsen, J. et al., "The mobilization of CD34 positive mononuclear cells after myocardial infarction is abolished by revascularization of the culprit vessel", International Journal of Cardiology, Aug. 3, 2005, vol. 103, No. 1, pp. 7-11.

Ott, I. et al., "Endothelial-like cells expanded from CD34+ blood cells improve left ventricular function after experimental myocardial infarction", The FASEB Journal, Jun. 2005, vol. 19, No. 8, pp. 992-994.

Thum, T. et al., "Mobilization of bone marrow-derived stem cells after myocardial infarction and left ventricular function: simply effects of optimized drug treatment?", European Heart Journal, Aug. 2005, vol. 26, No. 16, pp. 1685.

Yoshioka, T. et al., "Repair of infarcted myocardium mediated by transplanted bone marrow-derived CD34+ stem cells in a nonhuman primate model", Stem Cells, Mar. 2005, vol. 23, No. 3, pp. 355-364.

Antman et al., Heart Disease, 6th ed., E. Brunwald, Zipes D.P., Libby P. (eds.), Philadelphia, Saunders, 2001, pp. 1386-1399.

Paul, S. D. et al., "Geriatric patients with acute myocardial infarction: Cardiac risk factor profiles, presentation, thrombolysis, coronary interventions, and prognosis", American Heart Journal, 1996, vol. 131, No. 4, 710-715.

Pfeffer, M. A. et al., "Ventricular remodeling after myocardial infarction. Experimental observations and clinical implications", Circulation, 1990, vol. 81, No. 4, pp. 1161-1172.

Shieban, I. ey al., "Time course and determinants of left ventricular function recovery after primary angioplasty in patients with acute myocardial infarction", Journal of the American College of Cardiology, 2001, vol. 38, No. 2, pp. 464-471.

Braunwald, E. et al., "Congestive Heart Failure: Fifty Years of Progress", Circulation, 2000, vol. 102, pp. IV-14-IV-23.

Rich, M. W. et al., "Is age an independent predictor of early and late mortality in patients with acute myocardial infarction?", The American Journal of Medicine, 1992, vol. 92, No. 1, pp. 7-13

Ren, G. et al., "Morphological Characteristics of the Microvasculature in Healing Myocardial Infarcts", The Journal of Histochemistry and Cytochemistry, 2002, vol. 50, No. 1, pp. 71-79.

Hirai, T. et al., "Importance of collateral circulation for prevention of left ventricular aneurysm formation in acute myocardial infarction", Circulation, 1989, vol. 79, No. 4, pp. 791-796.

Ejiri, M. et al., "Development of collateral circulation after acute myocardial infarction; its role in preserving left ventricular function", Journal of Cardiology, 1990, vol. 20, pp. 31-37.

Frangogiannis, N. G. et al., "The inflammatory response in myocardial infarction", Cardiovascular Research, 2002, vol. 53, No. 1, pp. 31-47.

Bolli, R., "Basic and clinical aspects of myocardial stunning", Progress in Cardiovascular Diseases, 1998, vol. 40, No. 6, pp. 477-516.

Sakata, K. et al., "A clinical feature of myocardial stunning associated with acute myocardial infarction", Annals of Nuclear Medicine, 1994, vol. 8, No. 2, pp. 153-157.

Wollert, K. C. et al., "Intracoronary autologous bone-marrow cell transfer after myocardial infarction: the BOOST randomised controlled clinical trial", The Lancet, Jul. 2004, vol. 364, No. 9429, pp. 141-148.

Frangogiannis, N. G. et al., "Stem cell factor induction is associated with mast cell accumulation after canine myocardial ischemia and reperfusion", Circulation, Aug. 1998, vol. 98, No. 7, pp. 687-698.

Lefer, D. J. et al., "Oxidative stress and cardiac disease", The American Journal of Medicine, Sep. 2000, vol. 109, No. 4, pp. 315-323.

Frangogiannis, N. G. et al., "Resident cardiac mast cells degranulate and release preformed TNF-alpha, initiating the cytokine cascade in experimental canine myocardial ischemia/reperfusion", Circulation, Aug. 1998, vol. 98, No. 7, pp. 699-710.

Kurrelmeyer, K. M. et al., "Endogenous tumor necrosis factor protects the adult cardiac myocyte against ischemic-induced apoptosis in a murine model of acute myocardial infarction", Proc. Natl. Acad. Sci. U.S.A., May 2000, vol. 97, No. 10, pp. 5456-5461.

Lasky, L. A., "Selectins: interpreters of cell-specific carbohydrate information during inflammation", Science, Nov. 1992, vol. 258, No. 5084, pp. 964-969.

Ma, X. L. et al., "Monoclonal antibody to L-selectin attenuates neutrophil accumulation and protects ischemic reperfused cat myocardium", Circulation, 1993, vol. 88, No. 2, pp. 649-658.

Simpson, P. J. et al., "Reduction of experimental canine myocardial reperfusion injury by a monoclonal antibody (anti-Mo1, anti-CD11b) that inhibits leukocyte adhesion", Journal of Clinical Investigation, Feb. 1988, vol. 81, No. 2, pp. 624-629.

Entman, M. L. et al., "Neutrophil induced oxidative injury of cardiac myocytes. A compartmented system requiring CD11b/CD18-ICAM-1 adherence", Journal of Clinical Investigation, Oct. 1992, vol. 90, No. 4, pp. 1335-1345.

Frangogiannis, N. G. et al., "Induction and suppression of interferon-inducible protein 10 in reperfused myocardial infarcts may regulate angiogenesis", The FASEB Journal, Jun. 2001, vol. 15, No. 8, pp. 1428-1430.

Birdsall, H. H. et al., "Complement C5a, TGF-beta 1, and MCP-1, in sequence, induce migration of monocytes into ischemic canine myocardium within the first one to five hours after reperfusion", Circulation, Feb. 4, 1997, vol. 95, No. 3, pp. 684-692.

Frangogiannis, N. G. et al., "IL-10 is induced in the reperfused myocardium and may modulate the reaction to injury", The Journal of Immunology, Sep. 1, 2000, vol. 165, No. 5, pp. 2798-2808.

Fang, K. C. et al., "Mast cell expression of gelatinases A and B is regulated by kit ligand and TGF-beta", The Journal of Immunology, 1999, vol. 162, pp. 5528-5535.

Soeki, T. et al., "Serial changes in serum VEGF and HGF in patients with acute myocardial infarction", Cardiology, 2000, vol. 93, No. 3, pp. 168-174.

Bolognese, L. et al., "Left ventricular remodeling after primary coronary angioplasty: patterns of left ventricular dilation and long-term prognostic implications", Circulation, Oct. 29, 2002, vol. 106, No. 18, pp. 2351-2357.

Mann, D. L., "Mechanisms and models in heart failure: A combinatorial approach", Circulation, Aug. 31, 1999, vol. 100, No. 9, pp. 999-1008.

Shintani, S. et al., "Mobilization of endothelial progenitor cells in patients with acute myocardial infarction", Circulation, Jun. 12, 2001, vol. 103, No. 23, pp. 2776-2779.

Orlic, D. et al., "Mobilized bone marrow cells repair the infarcted heart, improving function and survival", Proc. Natl. Acad. Sci. U.S.A., Aug. 28, 2001, vol. 98, No. 18, pp. 10344-10349.

Jackson, K. A. et al., "Regeneration of ischemic cardiac muscle and vascular endothelium by adult stem cells", The Journal of Clinical Investigation, Jun. 2001, vol. 107, No. 11, pp. 1395-1402.

Edelberg, J. M. et al., "Young adult bone marrow-derived endothelial precursor cells restore aging-impaired cardiac angiogenic function", Circulation Research, May 31, 2002, vol. 90, No. 10, pp. E89-E93.

Saito, T. et al., "Myogenic Expression of Mesenchymal Stem Cells within Myotubes of mdx Mice in Vitro and in Vivo", Tissue Engineering, 1995, vol. 1, No. 4, pp. 327-343.

Kamihata, H. et al., "Implantation of bone marrow mononuclear cells into ischemic myocardium enhances collateral perfusion and regional function via side supply of angioblasts, angiogenic ligands, and cytokines", Circulation, Aug. 28, 2001, vol. 104, No. 9, pp. 1046-1052.

Hamano, K. et al., "Therapeutic angiogenesis induced by local autologous bone marrow cell implantation", The Annals of Thoracic Surgery, Apr. 2002, vol. 73, No., pp. 1210-1215.

Hamano, K. et al., "Local implantation of autologous bone marrow cells for therapeutic angiogenesis in patients with ischemic heart disease: clinical trial and preliminary results", Japanese Circulation Journal, Sep. 2001, vol. 65, No. 9, pp. 845-847.

Tse, H. F. et al., "Angiogenesis in ischaemic myocardium by intramyocardial autologous bone marrow mononuclear cell implantation", The Lancet, Jan. 4, 2003, vol. 361, No. 9351, pp. 47-49.

Stamm, C. et al., "Autologous bone-marrow stem-cell transplantation for myocardial regeneration", The Lancet, Jan. 4, 2003, vol. 361, No. 9351, pp. 45-46.

Kang, H. -J. et al., "Effects of intracoronary infusion of peripheral blood stem-cells mobilised with granulocyte-colony stimulating factor on left ventricular systolic function and restenosis after coronary stenting in myocardial infarction: the MAGIC cell randomised clinical trial", The Lancet, Mar. 6, 2004, vol. 363, pp. 746, 747; 751-756; 1732-1738.

Assmus, B. et al., "Transplantation of Progenitor Cells and Regeneration Enhancement in Acute Myocardial Infarction (Topcare-AMI)", Circulation, Dec. 10, 2002, vol. 106, No. 24, pp. 3009-3017.

Dobert, N. et al., "Transplantation of progenitor cells after reperfused acute myocardial infarction: evaluation of perfusion and myocardial viability with FDG-PET and thallium SPECT", European Journal of Nuclear Medicine and Molecular Imaging, vol. 31, No. 8, pp. 1146-1151.

Britten, M. B. et al., "Infarct remodeling after intracoronary progenitor cell treatment in patients with acute myocardial infarction (Topcare-AMI): mechanistic insights from serial contrast-enhanced magnetic resonance imaging", Circulation, Nov. 4, 2003, vol. 108, No. 18, pp. 2212-2218.

Yoon, Y. S. et al., "Unexpected severe calcification after transplantation of bone marrow cells in acute myocardial infarction", Circulation, Jun. 29, 2004, vol. 109, No. 25, pp. 3154-3157.

Yeh, E. T. et al., "Transdifferentiation of human peripheral blood CD34+-enriched cell population into cardiomyocytes, endothelial cells, and smooth muscle cells in vivo", Circulation, Oct. 28, 2003, vol. 108, No. 17, pp. 2070-2073.

Yin, A. H. et al., "AC133, a novel marker for human hematopoietic stem and progenitor cells", Blood, Dec. 15, 1997, vol. 90, No. 12, pp. 5002-5012.

Miraglia, S. et al., "A novel five-transmembrane hematopoietic stem cell antigen: isolation, characterization, and molecular cloning", Blood, Dec. 15, 1997, vol. 90, No. 12, pp. 5013-5021.

Reyes, M. et al., "Origin of endothelial progenitors in human postnatal bone marrow", J. Clinical Investigation, Feb. 2002, vol. 109, No. 3, pp. 337-346.

Hertenstein, B., "Monitoring of Bone Marrow Cell Homing in the Infarcted Human Myocardium ny PET", Blood Supplement, 2004, Abstract No. 2696.

Schiller, N. B. et al., "Recommendations for quantitation of the left ventricle by two-dimensional echocardiography. American Society of Echocardiography Committee on Standards, Subcommittee on Quantitation of Two-Dimensional Echocardiograms", The Journal of American Society of Echocardiography, Sep.-Oct. 1989, vol. 2, No. 5, pp. 358-367.

Pecora, A. L. et al., "CD34+CD33− cells influence days to engraftment and transfusion requirements in autologous blood stem-cell recipients", Journal of Clinical Oncology, Jun. 1998, vol. 16, No. 6, pp. 2093-2104.

Stiff, P. et al., "Autologous transplantation of ex vivo expanded bone marrow cells grown from small aliquots after high-dose chemotherapy for breast cancer", Blood, Mar. 15, 2000, vol. 95, No. 6, pp. 2169-2174.

Pecora, A. L. et al., "A phase II trial evaluating the safety and effectiveness of the AastromReplicell system for augmentation of low-dose blood stem cell transplantation", Bone Marrow Transplantation, Aug. 2001, vol. 28, No. 3, pp. 295-303.

Sousa, J. E. et al., "New frontiers in cardiology: drug-eluting stents: Part II", Circulation, May 13, 2003, vol. 107, No. 18, pp. 2383-2389.

Cerqueira, M. D. et al., "Safety profile of adenosine stress perfusion imaging: results from the Adenoscan Multicenter Trial Registry", Journal of the American College of Cardiology, Feb. 1994, vol. 23, No. 2, pp. 384-389.

Hattori, K. et al., "Placental growth factor reconstitutes hematopoiesis by recruiting VEGFR1(+) stem cells from bone-marrow microenvironment", Nature Medicine, Aug. 2002, vol. 8, No. 8, pp. 841-849.

Jo, D. Y. et al., "Chemotaxis of primitive hematopoietic cells in response to stromal cell-derived factor-1", Journal of Clinical Investigation, Jan. 2000, vol. 105, No. 1, pp, 101-111.

COMPOSITIONS AND METHODS OF VASCULAR INJURY REPAIR

CROSS-REFERENCES TO RELATED APPLICATIONS

This application is a divisional application of and claims the benefit of U.S. patent application Ser. No. 11/552,396, filed Oct. 24, 2006 now U.S. Pat. No. 7,794,705, which claims the benefit of U.S. Provisional Application Ser. No. 60/734,151, filed Nov. 7, 2005, both of which hereby are incorporated by reference in their entirety.

FIELD OF THE INVENTION

The present invention relates to compositions comprising a chemotactic hematopoietic stem cell product and methods of use thereof in repairing injury caused by vascular insufficiency, including infarcted myocardium, as well as other vascular conditions similar to or related to vascular insufficiency.

BACKGROUND OF THE INVENTION

Acute myocardial infarction remains common with a reported annual incidence of 1.1 million cases in the United States alone (Antman, E. M., Braunwald, E., Acute myocardial infarction, in Principles of Internal Medicine, 15$^{th}$ Ed., Braunwald, E. et al., Eds., New York: McGraw-Hill (2001)). Preclinical and clinical data demonstrate that following a myocardial infarction, the acute loss of myocardial muscle cells and the accompanying peri-infarct zone hypo-perfusion result in a cascade of events causing an immediate diminution of cardiac function, with the potential for long term persistence. The extent of myocardial cell loss is dependent on the duration of coronary artery occlusion, existing collateral coronary circulation and the condition of the cardiac microvasculature. Paul et al., Am. Heart J. 131: 710-15 (1996); Pfeffer, M. A., Braunwald, E., Circulation 81: 1161-72 (1990); Sheiban, I.e. al., J. Am. Coll. Cardiol. 38: 464-71 (2001); Braunwald E., Bristow, M. R., Circulation 102: IV-14-23 (2000); Rich et al., Am. J. Med. 92:7-13 (1992); Ren et al., J. Histochem. Cytochem. 49: 71-79 (2002); Hirai, T. et al., Circulation 79: 791-96 (1989); Ejiri, M. et al., J. Cardiology 20: 31-43 (1990). Because myocardial cells have virtually no ability to regenerate, myocardial infarction leads to permanent cardiac dysfunction due to contractile-muscle cell loss and replacement with nonfunctioning fibrotic scarring. Frangogiannis, N. G., et al., Cardiovascular Res. 53(1): 31-47 (2002). Moreover, compensatory hypertrophy of viable cardiac muscle leads to microvascular insufficiency that results in further demise in cardiac function by causing myocardial muscle hibernation and apoptosis of hypertrophied myocytes in the peri-infarct zone.

Among survivors of myocardial infarction, residual cardiac function is influenced most by the extent of ventricular remodeling (meaning changes in size, shape, and function, typically a decline in function, of the heart after injury). Alterations in ventricular topography (meaning the shape, configuration, or morphology of a ventricle) occur in both infarcted and healthy cardiac tissue after myocardial infarction. Pfeffer, M. A., Braunwald, E., Circulation 81: 1161-72 (1990). Ventricular dilatation (meaning a stretching, enlarging or spreading out of the ventricle) causes a decrease in global cardiac function and is affected most by the infarct size, infarct healing and ventricular wall stresses. Recent efforts to minimize remodeling have been successful by limiting infarct size through rapid reperfusion (meaning restoration of blood flow) using thrombolytic agents and mechanical interventions, including, but not limited to, placement of a stent, along with reducing ventricular wall stresses by judicious use of pre-load therapies and proper after-load management. Id. Regardless of these interventions, a substantial percentage of patients experience clinically relevant and long-term cardiac dysfunction after myocardial infarction. Sheiban, I. et al., J. Am. Coll. Cardiol. 38: 464-71 (2001). Despite revascularization of the infarct related artery circulation and appropriate medical management to minimize ventricular wall stresses, a significant percentage of patients experience ventricular remodeling, permanent cardiac dysfunction, and consequently remain at an increased lifetime risk of experiencing adverse cardiac events, including death. Paul et al., Am. Heart J. 131: 710-15 (1996); Pfeffer, M. A., Braunwald, E., Circulation 81: 1161-72 (1990).

At the cellular level, immediately following a myocardial infarction, transient generalized cardiac dysfunction uniformly occurs. In the setting of a brief (i.e., lasting three minutes to five minutes) coronary artery occlusion, energy metabolism is impaired, leading to demonstrable cardiac muscle dysfunction that can persist for up to 48 hours despite immediate reperfusion. This so-called "stunned myocardium phenomenon" occurs subsequent to or after reperfusion and is thought to be a result of reactive oxygen species. The process is transient and is not associated with an inflammatory response. Frangogiannis, N. G., et al., Cardiovascular Res. 53(1): 31-47 (2002). After successful revascularization, significant recovery from stunning occurs within three to four days, although complete recovery may take much longer. Boli, R., Prog. Cardiovascular Disease 40(6): 477-515 (1998); Sakata, K. et al., Ann. Nucleic Med. 8: 153-57 (1994); Wollert, K. C. et al., Lancet 364: 141-48 (2004).

Coronary artery occlusion of more significant duration, i.e., lasting more than five minutes, leads to myocardial ischemia (i.e., an insufficient blood flow to the heart's muscle mass) and is associated with a significant inflammatory response that begins immediately after reperfusion and can last for up to several weeks. Frangogiannis, N. G., et al., Cardiovascular Res. 53(1): 31-47 (2002); Frangogiannis, N. G. et al., Circulation 98: 687-798 (1998).

The inflammatory process following reperfusion is complex. Initially it contributes to myocardial damage but later leads to healing and scar formation. This complex process appears to occur in two phases. In the first so-called "hot" phase (within the first five days), reactive oxygen species (in the ischemic myocardial tissue) and complement activation generate a signal chemotactic for leukocytes (chemotaxis is the directed motion of a motile cell, organism or part towards environmental conditions it deems attractive and/or away from surroundings it finds repellent) and initiate a cytokine cascade. Lefer, D. J., Granger, D. N., Am. J. Med. 4:315-23 (2000); Frangogiannis, N. G., et al., Circulation 7:699-710 (1998). Mast cell degranulation, tumor necrosis factor alpha (TNF-α) release, and increased interleukin-6 (IL-6), intercellular adhesion molecule 1 ("ICAM-1" or CD-54, a receptor typically expressed on endothelial cells and cells of the immune system), selectin (L, E and P) and integrin (CD11a, CD11b and CD18) expression all appear to contribute to neutrophil accumulation and degranulation in ischemic myocardium. Frangogiannis, N. G. et al., Circulation 7: 699-710 (1998), Kurrelmeyer, K. M, et al., Proc. Nat'l Acad. Sci. 10: 5456-61 (2000); Lasky, L. A., Science 258: 964-69 (1992); Ma, X. L., et al., Circulation 88(2): 649-58 (1993); Simpson, P. J. et al., J. Clin. Invest. 2: 624-29 (1998). Neutrophils contribute significantly to myocardial cell damage and death through microvascular obstruction and activation of neutrophil respiratory burst pathways after ligand-specific adhesion to cardiac myocytes. Entman, M. L., et al., J. Clin. Invest. 4: 1335-45 (1992). During the "hot" phase, angiogenesis is inhibited due to the release of angiostatic substances, including interferon gamma-inducible protein (IP 10). Frangogiannis, N. G., et al., FASEB J. 15: 1428-30 (2001).

In the second phase, the cardiac repair process begins (about day 6 to about day 14), which eventually leads to scar formation (about day 14 to about day 21) and subsequent ventricular remodeling (about day 21 to about day 90). Soon after reperfusion, monocytes infiltrate the infarcted myocardium. Attracted by complement (C5a), transforming growth factor B1 ("TGF-B1") and monocyte chemotactic protein 1 ("MCP-1"), monocytes differentiate into macrophages that initiate the healing process by scavenging dead tissue, regulating extracellular matrix metabolism, and inducing fibroblast proliferation. Birdshall, H. H., et al., Circulation 3: 684-92 (1997). Secretion of interleukin 10 (IL-10) by infiltrating lymphocytes also promotes healing by down-regulating inflammatory cytokines and influencing tissue remodeling. Frangogiannis, N. G. et al., J. Immunol. 5:2798-2808 (2000). Mast cells also appear to be involved in the later stages of myocardial repair by participating in the formation of fibrotic scar tissue. Stem Cell Factor (SCF) is a potent attractor of mast cells. SCF mRNA has been shown to be up-regulated in ischemic myocardial segments in a canine model of myocardial infarction and thus may contribute to mast cell accumulation at ischemic myocardial sites. Frangogiannis, N. G. et al., Circulation 98: 687-798 (1998). Mast cell products (including TGF-B, basic fibroblast growth factor (bFGF), vascular endothelial growth factor (VEGF) and gelatinases A and B) induce fibroblast proliferation, influence extracellular matrix metabolism, and induce angiogenesis. Fang, K. C., et al., J. Immunol. 162: 5528-35 (1999); Takeshi, S., et al., Cardiology 93: 168-74 (2000).

Following a myocardial infarction, neoangiogenesis occurs after the "hot" phase of the inflammatory process subsides (about day 5) coincident with rising levels of VEGF (VEGF peaks at about day 7 and gradually subsides to baseline at about day 14 to about day 21). During this phase of the healing process, endothelial precursor cells (EPCs) are mobilized and recruited to the infarct site. Shinitani, S., et al., Circulation 103: 2776-79 (2001). Without being limited by theory, it has been suggested that the chemokine stromal cell derived factor-1 (SDF-1), which is the ligand for the CXCR-4 chemokine receptor expressed by CD34+ cells, also plays a role in homing of cells to areas of ischemic damage. Ceredini, D. J., et al., Nature Medicine 10: 858-63 (2004); Askari, A., et al., Lancet 362: 697-703 (2003); Yamaguchi, J. et al., Circulation 107: 1322-34 (2003). While it is known that SDF-1 plays a role in hematopoiesis and is involved in migration, homing and survival of hematopoietic progenitors, and while SDF-1 has been implicated in ischemic neovascularization in vivo by augmenting EPC recruitment to ischemic sites (Yamaguchi et al. Circulation 107:1322-1328 (2003), SDF-1's role in neoangiogenesis is not certain. There is suggestive evidence implicating SDF-1. For example, SDF-1 gene expression is upregulated during hypoxia, a deficiency of oxygen in the tissues, by hypoxia inducible factor-1. Furthermore, CD34+ cells are capable of homing to areas of ischemia, rich in SDF-1, including infarcted myocardium. Askari et al., Lancet 362: 697-703 (2003). Moreover, virtually all $CD34^+CXCR-4^+$ cells co-express VEGF-2 and therefore migrate in response to VEGF as well as SDF-1. Peichev M., et al., Blood 95: 952-58 (2000). $CD34^+CXCR-4^+$ VEGF-1 cells, once recruited, are capable of contributing to neoangiogenesis. Yamaguchi, J. et al., Circulation 107: 1322-34 (2003).

To date, no ideal therapy exists for preventing the long term adverse consequences of vascular insufficiency, particularly the significant vascular insufficiency that results in a myocardial infarction. While large vessel revascularization (meaning the successful placement of a stent) seems promising, studies to date have shown such applications to be insufficient in addressing increased demands posed by compensatory myocardial hypertrophy. As a result, infarct extension and fibrous replacement commonly occur, regardless of large vessel revascularization, appropriate medical management of ventricular wall stresses, and potential natural, albeit suboptimal, CD34+ cell-mediated neoangiogenesis (one of the theories relating to the underlying cause of myocardial infarction is that the ability to mobilize these cells may be biologically limited).

Intense interest has developed in evaluating the ability of endothelial and myocardial precursor cells to limit damage to the myocardium after infarction and to limit or prevent ventricular remodeling. Significant preclinical data and some clinical data demonstrate the safety and potential of cell therapy using a variety of cell precursors (particularly hematopoietic cells) to contribute to neoangiogenesis, limited cardiac myogenesis (principally by fusion), and muscle preservation in the myocardial infarct zone. See, e.g., Jackson, et al., J. Clin. Invest. 107: 1395-1402 (2001); Edelberg, J. M., et al., Cir. Res. 90: e89-e93 (2002); Schichinger, V. et al., New Engl. J. Med. 355 (12): 1210-21 (2006) (using bone marrow-derived progenitor cells); Assmus, B. et al., New Engl. J. Med. 355 (12) 1222-32 (2006) (using bone marrow-derived progenitor cells), but see Lunde, K. et al., New Eng. J. Med. 355 (12): 1199-209 (2006) (using bone marrow-derived progenitor cells).

Bone marrow consists of a variety of precursor and mature cell types, including hematopoietic cells (the precursors of mature blood cells) and stromal cells (the precursors of a broad spectrum of connective tissue cells), both of which appear to be capable of differentiating into other cell types. Wang, J. S. et al., J. Thorac. Cardiovasc. Surg. 122: 699-705 (2001); Tomita, S. et al., Circulation 100 (Suppl. II): 247-256 (1999); Saito, T. et al., Tissue Eng. 1: 327-43 (1995). Unmodified (i.e., not fractionated) marrow or blood-derived cells have been used in several clinical studies, for example, Hamano, K. et al., Japan Cir. J. 65: 845-47 (2001); Strauer, B. E., et al., Circulation 106: 1913-18 (2002); Assmus, et al., Circulation 106: 3009-3017 (2002); Dobert, N. et al., Eur. J. Nucl. Med. Mol. Imaging, 8: 1146-51 (2004); Wollert, K. C. et al., Lancet 364: 141-48 (2004). Since the mononuclear fraction of bone marrow contains stromal cells, hematopoietic precursors, and endothelial precursors, the relative contribution of each of these populations to the observed effects, if any, remains unknown.

CD34 is a hematopoietic stem cell antigen selectively expressed on hematopoietic stem and progenitor cells derived from human bone marrow, blood and fetal liver. Yin et al., Blood 90: 5002-5012 (1997); Miaglia, S. et al., Blood 90: 5013-21 (1997). Cells that express CD34 are termed $CD34^+$. Stromal cells do not express CD34 and are therefore termed $CD34^-$. $CD34^+$ cells isolated from human blood may be capable of differentiating into cardiomyocytes, endothelial cells, and smooth muscle cells in vivo. See Yeh, et al., Circulation 108: 2070-73 (2003). $CD34^+$ cells represent approximately 1% of bone marrow derived nucleated cells; CD34 antigen also is expressed by immature endothelial cell precursors; mature endothelial cells do not express CD34+.

Peichev, M. et al., Blood 95: 952-58 (2000). In vitro, CD34+ cells derived from adult bone marrow give rise to a majority of the granulocyte/macrophage progenitor cells (CFU-GM), some colony-forming units-mixed (CFU-Mix) and a minor population of primitive erythroid progenitor cells (burst forming units, erythrocytes or BFU-E). Yeh, et al., Circulation 108: 2070-73 (2003). CD34+ cells also may have the potential to differentiate into or to contribute to the development of new myocardial muscle, albeit at low frequency.

Techniques have been developed using immunomagnetic bead separation to isolate a highly purified and viable population of CD34+ cells from bone narrow mononuclear cells. See U.S. Pat. Nos. 5,536,475, 5,035,994, 5,130,144, 4,965,205, the contents of each of which is incorporated herein by reference. Two clinical studies support the clinical application of bone marrow derived CD34+ cells after myocardial infarction. See C. Stamm, et al., Lancet 361: 45-46 (2003); Herenstein, B. et al., Blood Supplement, Abs. 2696 (2004).

To date, however, no ideal therapy exists for preventing the long-term adverse consequences of vascular insufficiency, particularly vascular insufficiency that produces myocardial infarction.

The present invention addresses the question of whether a composition comprising a chemotactic hematopoietic stem cell product comprising an enriched population of isolated CD34+ cells containing a subpopulation of cells having chemotactic activity can be manufactured, remain stable for a commercially viable period, and be delivered to a subject in need thereof so that potent cells can home to and repair sites of vascular insufficiency, including infarcted myocardium.

SUMMARY OF THE INVENTION

The present invention relates to pharmaceutical compositions comprising a chemotactic hematopoietic stem cell product comprising an enriched population of CD34+ cells containing a subpopulation of cells having chemotactic activity, methods of preparing these compositions and use of these compositions to treat or repair vascular injury, including infarcted myocardium. The present invention provides a pharmaceutical composition for repairing a vascular injury in a subject comprising: (a) a therapeutically effective amount of a sterile isolated chemotactic hematopoietic stem cell product, the chemotactic hematopoietic stem cell product comprising an enriched population of isolated CD34+ cells having a subpopulation of potent cells having chemotactic activity; and (b) a stabilizing amount of serum, wherein the composition is administered to the subject parenterally through a catheter, and wherein the subpopulation of potent cells having chemotactic activity when passed through the catheter remains potent. According to one embodiment, the enriched population of isolated CD34+ cells in the chemotactic hematopoietic stem cell product of the composition is purified from bone marrow acquired from the subject. According to another embodiment, the enriched population of isolated CD34+ cells is at least 70% pure. According to another embodiment, the enriched population of isolated CD34+ cells is at least 70% viable for at least about 24 hours following acquisition of the enriched population of isolated CD34+ cells. According to another embodiment, the enriched population of isolated CD34+ cells is at least 70% viable for at least about 48 hours following acquisition of the enriched population of isolated CD34+ cells. According to another embodiment, enriched population of isolated CD34+ cells is at least 70% viable for at least about 72 hours following acquisition of the enriched population of isolated CD34+ cells. According to another embodiment, the therapeutically effective amount of the chemotactic hematopoietic stem cell product comprises a minimum number of isolated CD34+ hematopoietic stem cells containing a subpopulation of at least $0.5 \times 10^6$ potent CD34+ cells having CXCR-4 mediated chemotactic activity. According to another embodiment, the enriched CD34+ cells are capable of forming hematopoietic colonies in vitro for at least about 24 hours following acquisition of the enriched CD34+ cells. According to another embodiment, the enriched CD34+ cells are capable of forming hematopoietic colonies in vitro for at least about 48 hours following acquisition of the enriched CD34+ cells. According to another embodiment, the enriched CD34+ cells are capable of forming hematopoietic colonies in vitro for at least about 72 hours following acquisition of the enriched CD34+ cells. According to another embodiment, the serum is human serum autologous to the patient or synthetic serum. According to another embodiment, the stabilizing amount of serum is at least about 10% (v/v). According to another embodiment, at least 2% of the chemotactic activity of the subpopulation of potent cells is retained by the subpopulation of potent cells for at least 24 hours following acquisition of the enriched population of isolated CD34+ cells. According to another embodiment, at least 2% of the chemotactic activity of the subpopulation of potent cells is retained by the subpopulation of potent cells for at least 48 hours following acquisition of the enriched population of isolated CD34+ cells. According to another embodiment, at least 2% of the chemotactic activity of the subpopulation of potent cells is retained by the subpopulation of potent cells for at least 72 hours following acquisition of the enriched population of isolated CD34+ cells. According to another embodiment, the enriched population of isolated CD34+ cells containing a subpopulation of potent cells having chemotactic activity is at least 70% pure, is at least about 70% viable, and is able to form hematopoietic colonies in vitro for at least about 24 hours following acquisition of the enriched population. According to another embodiment, the enriched population of isolated CD34+ cells containing a subpopulation of potent cells having chemotactic activity is at least 70% pure, is at least about 70% viable, and is able to form hematopoietic colonies in vitro for at least about 48 hours following acquisition of the enriched population. According to another embodiment, the enriched population of isolated CD34+ cells containing a subpopulation of potent cells having chemotactic activity is at least 70% pure, is at least about 70% viable, and is able to form hematopoietic colonies in vitro for at least about 72 hours following acquisition of the enriched population. According to another embodiment, the subject is a revascularized myocardial infarction patient. According to another embodiment, the composition is administered through the catheter intravascularly to an infarct-related artery. According to another embodiment, the catheter is a flow control catheter. According to another embodiment, the catheter is a balloon catheter. According to another embodiment, the catheter has an internal diameter of at least 0.36 mm. According to another embodiment, the composition is administered through the catheter intravascularly by means of an intravascular delivery apparatus. According to another embodiment, the composition is administered through the catheter into myocardium. According to another embodiment, the pharmaceutical composition further comprises at least about 0.5% albumin. According to another embodiment, the pharmaceutical composition further includes at least one compatible active agent. According to another embodiment, the active agent is selected from the group consisting of an angiotensin converting enzyme inhibitor, a beta-blocker, a diuretic, an anti-arrhythmic agent, an anti-anginal agent, a vasoactive agent, an anticoagulant agent, a fibrinolytic agent, and a hypercholesterolemic agent. According to another embodiment, sterility of the chemotactic hematopoietic cell product of the composition is confirmed by a method comprising the steps: (a) centrifuging the cell product to form a separated cell product comprising a pellet comprising the enriched population of isolated CD34+ cells and a supernatant; (b) removing the supernatant of the separated cell product without disturbing the cell pellet of the separated cell product; (c) analyzing the sterility of the supernatant of the separated cell product; and (d) thereby determining the sterility of the cell pellet of the separated cell product.

The present invention further provides a method of preparing a pharmaceutical composition for intravascular delivery to a subject having a vascular injury, the pharmaceutical composition comprising a sterile chemotactic hematopoietic stem cell product comprising an enriched population of isolated CD34+ cells containing a subpopulation of potent cells having chemotactic activity, the method comprising the steps: (a) acquiring a preparation comprising an enriched population of potent CD34+ cells from the subject under sterile conditions by a chemotactic cell acquisition process, (b) optionally transporting the preparation to a processing facility; (c) sterilely purifying CD34+ cells containing a subpopulation of potent cells having chemotactic activity from the preparation; (d) sterilely formulating the purified CD34+ cells containing a subpopulation of potent cells having chemotactic activity to form the chemotactic hematopoietic cell product; (e) sterilely formulating the sterile chemotactic hematopoietic stem cell product to form a pharmaceutical composition; (e) assessing sterility of the pharmaceutical composition; (f) releasing the sterile pharmaceutical composition as eligible for infusion into the subject; (g) loading a therapeutic amount of the pharmaceutical composition into an intravascular delivery apparatus; and (h) optionally transporting the delivery apparatus containing the therapeutically effective amount of the sterile pharmaceutical composition to a cardiac catheterization facility for intravascular infusion into the subject. According to one embodiment, the method optionally further comprises the step of storing the acquired preparation between steps (a) and (b). According to another embodiment, purifying step (c) of the method is initiated within about 12 hours to about 24 hours of completion of acquiring step (a). According to another embodiment, purifying step (c) of the method is initiated within about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours of completion of acquiring step (a). According to another embodiment, releasing step (f) of the method proceeds only if the sterile formulated cell product is to be infused into the subject within about 48 hours to about 72 hours of completion of acquiring step (a). According to another embodiment, releasing step (f) of the method proceeds only if the sterile formulated cell product is to be infused into the subject within about 48 hours, about 49 hours, about 50 hours, about 51 hours, about 52 hours, about 53 hours, about 54 hours, about 55 hours, about 56 hours, about 57 hours, about 58 hours, about 59 hours, about 60 hours, about 61 hours, about 62 hours, about 63 hours, about 64 hours, about 65 hours, about 66 hours, about 67 hours, about 68 hours, about 69 hours, about 70 hours, about 71 hours or about 72 hours of completion of acquiring step (a). According to another embodiment, purifying step (c) of the method is initiated within about 12 hours to about 24 hours of completion of acquiring step (a), and releasing step (f) proceeds only if the sterile pharmaceutical composition is to be infused into the subject within about 48 hours to about 72 hours of completion of acquiring step (a). According to another embodiment, purifying step (c) of the method is initiated within about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours of completion of acquiring step (a), and releasing step (f) of the method proceeds only if the sterile pharmaceutical composition is to be infused into the subject within about 48 hours, about 49 hours, about 50 hours, about 51 hours, about 52 hours, about 53 hours, about 54 hours, about 55 hours, about 56 hours, about 57 hours, about 58 hours, about 59 hours, about 60 hours, about 61 hours, about 62 hours, about 63 hours, about 64 hours, about 65 hours, about 66 hours, about 67 hours, about 68 hours, about 69 hours, about 70 hours, about 71 hours or about 72 hours of completion of acquiring step (a). According to another embodiment, the chemotactic cell acquisition process in step (a) of the method is a mini-bone marrow harvesting technique. According to another embodiment, acquiring step (a) of the mini-bone marrow harvesting technique further comprises the steps: (i) preloading harvesting syringes with heparin prior to harvesting bone marrow from the subject; (ii) aspirating the bone marrow from a left posterior iliac crest and a right posterior iliac crest of the subject using the harvesting syringes and a mini-bone marrow harvest technique to form harvested bone marrow; and (iii) infusing the harvested bone marrow into a collecting bag. According to another embodiment, the harvesting syringes in step (i) and the collecting bag in step (iii) contain a preservative free heparinized solution. According to another embodiment, the final concentration of heparin in the preservative free heparinized solution is about 20 units per ml to about 25 units per ml. According to another embodiment, transporting step (b) of the method further comprises the steps: (i) placing the harvested bone marrow in a collection bag; (ii) placing the collection bag in a secondary bag; (ii) preparing an open shipping container; (iii) placing the secondary bag containing the collection bag in the open shipping container; (iv) sealing the shipping container; and (v) shipping the shipping container to the processing facility. According to another embodiment, the enriched population of isolated CD34+ cells in step (c) of the method is at least 70% pure. According to another embodiment, the enriched population of isolated CD34+ cells is at least 70% viable for at least about 24 hours following acquisition of the enriched population of isolated CD34+ cells in step (a) of the method. According to another embodiment, the enriched population of isolated CD34+ cells is at least 70% viable for at least about 48 hours following acquisition of the enriched population of isolated CD34+ cells in step (a) of the method. According to another embodiment, the enriched population of isolated CD34+ cells is at least 70% viable for at least about 72 hours following acquisition of the enriched population of isolated CD34+ cells in step (a) of the method. According to another embodiment, the enriched CD34+ cells are capable of forming hematopoietic colonies in vitro for at least about 24 hours following acquisition of the enriched CD34+ cells in step (a) of the method. According to another embodiment, the enriched CD34+ cells are capable of forming hematopoietic colonies in vitro for at least about 48 hours following acquisition of the enriched CD34+ cells in step (a) of the method. According to another embodiment, the enriched CD34+ cells are capable of forming hematopoietic colonies in vitro for at least about 72 hours following acquisition of the enriched CD34+ cells in step (a) of the method. According to another embodiment, at least 2% of the chemotactic activity of the subpopulation of potent cells is retained by the subpopulation of potent cells for at least 24 hours following acquisition of the enriched population of isolated CD34+ cells in step (a) of the method. According to another embodiment, at least 2% of the chemotactic activity of the subpopulation of potent cells is retained by the subpopulation of potent cells for at least 48 hours following acquisition of the enriched population of isolated CD34+ cells in step (a) of the method. According to another embodiment, at least 2% of the chemotactic activity of the subpopulation of potent cells is retained by the subpopulation of potent cells for at least 72 hours following acquisition of the enriched population of isolated CD34+ cells in step (a) of the method. According to another embodiment, the enriched population of isolated CD34+ cells containing a subpopulation of potent cells having chemotactic activity is at least 70% pure, is at least about 70% viable, and is able to form hematopoietic colonies in vitro for at least about 24 hours following acquisition of the enriched population of isolated CD34+ cells in step (a) of the method. According to another embodiment, the enriched population of isolated CD34+ cells containing a subpopulation of potent cells having chemotactic activity is at least 70% pure, is at least about 70% viable, and is able to form hematopoietic colonies in vitro for at least about 48 hours following acquisition of the enriched population of isolated CD34+ cells in step (a) of the method. According to another embodiment, the enriched population of isolated CD34+ cells containing a subpopulation of potent cells having chemotactic activity is at least 70% pure, is at least about 70% viable, and is able to form hematopoietic colonies in vitro for at least about 72 hours following acquisition of the enriched population of isolated CD34+ cells in step (a) of the method. According to another embodiment, the therapeutically effective amount of the chemotactic hematopoietic stem cell product in the pharmaceutical composition of step (g) of the method comprises a minimum number of CD34+ hematopoietic stem cells containing a subpopulation of at least $0.5 \times 10^6$ CD34+ potent cells having CXCR-4 mediated chemotactic activity. According to another embodiment, the confirming sterility step (e) of the method further comprises the steps of (i) centrifuging the formulated cell product to form separated cell product comprising a cell pellet comprising the enriched population of isolated CD34+ cells and a supernatant, (ii) sterilely removing the supernatant of the separated cell product without disturbing the cell pellet of the separated cell product; (iii) analyzing whether the supernatant of the separated cell product is contaminated by a microbe; and (iv) thereby determining the sterility of the cell pellet of the separated cell product. According to another embodiment, the intravascular delivery apparatus of step (g) of the method comprises (i) an infusion syringe attached to a sterile four-way stopcock, wherein the infusion syringe contains the pharmaceutical composition; (ii) a flushing syringe attached to the sterile four-way stopcock containing a flushing solution; and (iii) a catheter attached to the delivery apparatus by the sterile four-way stopcock for delivery of the pharmaceutical composition to the subject. According to another embodiment, the catheter is a flow control catheter. According to another embodiment, the catheter is a balloon dilatation catheter. According to another embodiment, the catheter has an internal diameter of at least 0.36 mm. According to another embodiment, the subject in need thereof is a revascularized myocardial infarction patient. According to another embodiment, the pharmaceutical composition is delivered to the subject by infusion of the composition through the catheter to an infarct related artery. According to another embodiment, the pharmaceutical composition is administered through the catheter into myocardium.

Moreover, the present invention provides a method of treating or repairing a vascular injury in a subject in need thereof, the method comprising the step of administering to the subject parenterally through a catheter a sterile pharmaceutical composition comprising: (a) a therapeutically effective amount of a sterile chemotactic hematopoietic stem cell product, the chemotactic hematopoietic stem cell product comprising an enriched population of isolated CD34+ cells containing a subpopulation of potent cells having chemotactic activity; and (b) a stabilizing amount of serum, wherein the subpopulation of potent cells having chemotactic activity when passed through the catheter remains potent. According to one embodiment, the enriched population of isolated CD34+ cells is at least 70% pure. According to another embodiment, the enriched population of isolated CD34+ cells is at least 70% viable for at least about 24 hours following acquisition of the enriched population of isolated CD34+ cells. According to another embodiment, the enriched population of isolated CD34+ cells is at least 70% viable for at least about 48 hours following acquisition of the enriched population of isolated CD34+ cells. According to another embodiment, the enriched population of isolated CD34+ cells is at least 70% viable for at least about 72 hours following acquisition of the enriched population of isolated CD34+ cells. According to another embodiment, the therapeutically effective amount of the chemotactic hematopoietic stem cell product comprises a minimum number of isolated CD34+ hematopoietic stem cells containing a subpopulation of at least $0.5 \times 10^6$ potent CD34+ cells having CXCR-4 mediated chemotactic activity. According to another embodiment, the enriched CD34+ cells are capable of forming hematopoietic colonies in vitro for at least about 24 hours following acquisition of the enriched CD34+ cells. According to another embodiment, the enriched CD34+ cells are capable of forming hematopoietic colonies in vitro for at least about 48 hours following acquisition of the enriched CD34+ cells. According to another embodiment, the enriched CD34+ cells are capable of forming hematopoietic colonies in vitro for at least about 72 hours following acquisition of the enriched CD34+ cells. According to another embodiment, at least 2% of the chemotactic activity of the subpopulation of potent cells is retained by the subpopulation of potent cells for at least 24 hours following acquisition of the enriched population of isolated CD34+ cells. According to another embodiment, at least 2% of the chemotactic activity of the subpopulation of potent cells is retained by the subpopulation of potent cells for at least 48 hours following acquisition of the enriched population of isolated CD34+ cells. According to another embodiment, at least 2% of the chemotactic activity of the subpopulation of potent cells is retained by the subpopulation of potent cells for at least 72 hours following acquisition of the enriched population of isolated CD34+ cells. According to another embodiment, the enriched population of isolated CD34+ cells containing a subpopulation of potent cells having chemotactic activity is at least 70% pure, is at least about 70% viable, and is able to form hematopoietic colonies in vitro for at least about 24 hours following acquisition of the enriched population. According to another embodiment, the enriched population of isolated CD34+ cells containing a subpopulation of potent cells having chemotactic activity is at least 70% pure, is at least about 70% viable, and is able to form hematopoietic colonies in vitro for at least about 48 hours following acquisition of the enriched population. According to another embodiment, the enriched population of isolated CD34+ cells containing a subpopulation of potent cells having chemotactic activity is at least 70% pure, is at least about 70% viable, and is able to form hematopoietic colonies in vitro for at least about 72 hours following acquisition of the enriched population. According to another embodiment, the serum is human serum autologous to the subject or a synthetic serum. According to another embodiment, the stabilizing amount of serum is at least about 10% (v/v). According to another embodiment, the subject is a revascularized myocardial infarction patient. According to another embodiment, the method further comprising the step of delivering the composition intravascularly to an infarct related artery by means of an intravascular delivery apparatus. According to another embodiment, the intravascular delivery apparatus comprises (i) an infusion syringe attached to a sterile four-way stopcock, wherein the infusion syringe contains the pharmaceutical composition; (ii) a flushing syringe attached to the sterile four-way stopcock containing a flushing solution; and (iii) a catheter attached to the delivery apparatus by the sterile four-way stopcock for delivery of the pharmaceutical composition to the subject. According to another embodiment, the catheter is a flow control catheter. According to another embodiment, the catheter is a balloon dilatation catheter. According to another embodiment, the catheter has an internal diameter of at least 0.36 mm. According to another embodiment, the pharmaceutical composition is delivered to the subject during a specific time interval defined by a first time and a second time. According to another embodiment, the first time is at least about 5 days post-infarction and the second time is less than about 14 days post-infarction. According to another embodiment, the first time is after peak inflammatory cytokine cascade production in the infracted area. According to another embodiment, the second time is before myocardial scar formation in the infracted area. According to another embodiment, the composition is administered through the catheter intravascularly by means of an intravascular delivery apparatus. According to another embodiment, the composition is administered through the catheter into myocardium. According to another embodiment, the pharmaceutical composition further includes at least one compatible active agent. According to another embodiment, the active agent is selected from the group consisting of an angiotensin converting enzyme inhibitor, a beta-blocker, a diuretic, an anti-arrhythmic agent, an anti-anginal agent, a vasoactive agent, an anticoagulant agent, a fibrinolytic agent, and a hypercholesterolemic agent.

In addition, the present invention provides a method of assessing sterility of a clinically useful isolated cell product having a limited volume, the method comprising the steps: (a) sterilely separating cellular components of the isolated cell product from noncellular components; and (b) testing the noncellular components for microbial contamination, thereby determining the sterility of the clinically useful isolated cell product. According to one embodiment, in step (a) of the method the cellular components are separated from noncellular components by centrifugation. According to another embodiment, the cellular components form a cell pellet upon centrifugation of the isolated cell product. According to another embodiment, the noncellular components form a supernatant upon centrifugation of the isolated cell product. According to another embodiment, the isolated cell product is a chemotactic hematopoietic stem cell product. According to another embodiment, the chemotactic hematopoietic stem cell product comprises an enriched population of isolated CD34+ cells containing a subpopulation of potent cells having CXCR-4 mediated chemotactic activity. According to another embodiment, after sterility of the supernatant is confirmed, a therapeutically effective amount of the sterile chemotactic hematopoietic stem cell product is administered to a subject intravascularly to treat or repair a vascular injury.

According to another embodiment, the sterile chemotactic hematopoietic stem cell product is administered through a catheter. According to another embodiment, the subject is a revascularized myocardial infarction patient. According to another embodiment, the vascular injury is a vascular insufficiency. According to another embodiment, the vascular insufficiency affects at least one coronary artery.

DETAILED DESCRIPTION OF THE INVENTION

Figure 1:
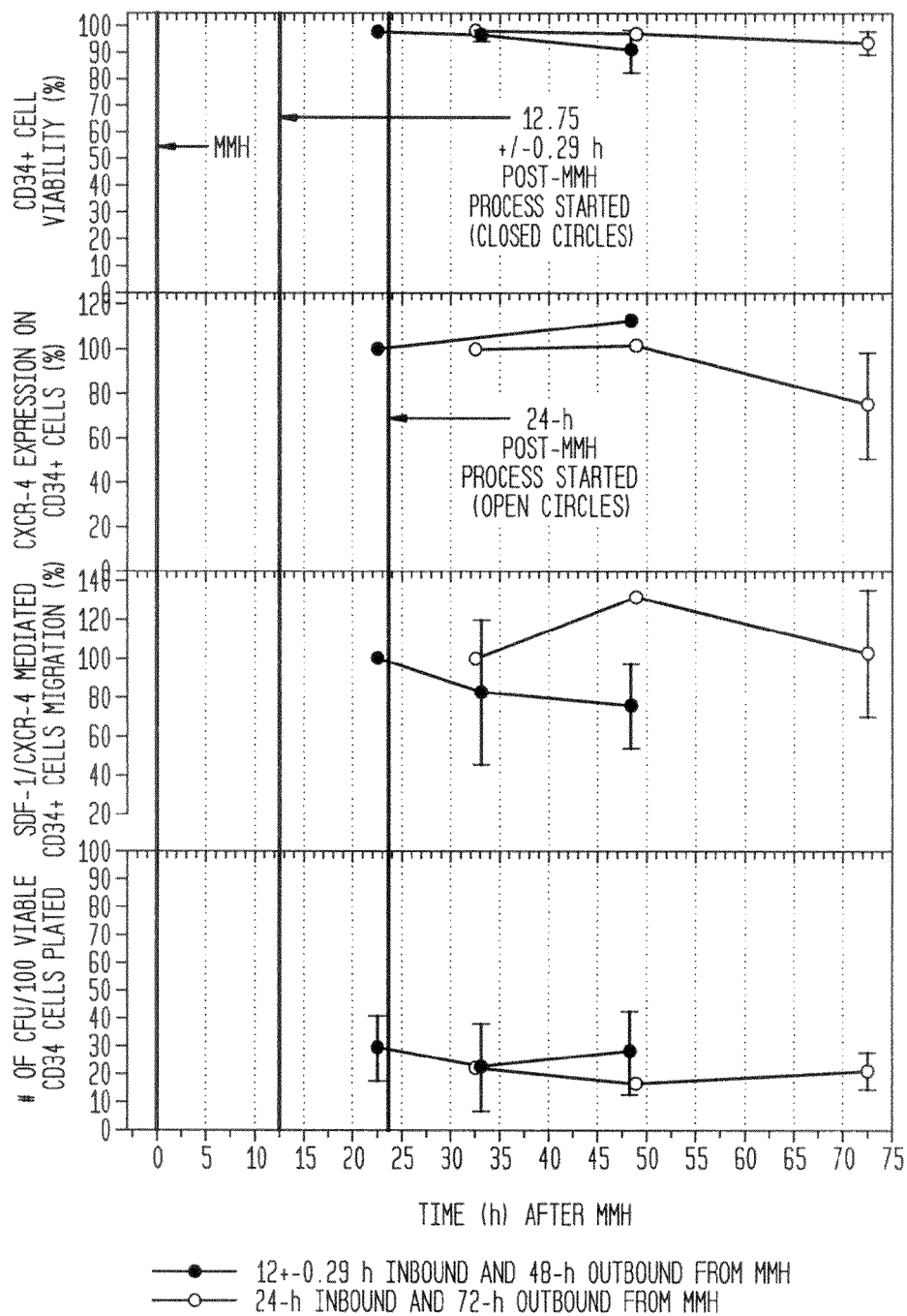
FIG. 1 shows that the functional viability of the chemotactic hematopoietic cell product of the present invention at 72 hours is equivalent to that at 48 hours.

The following definitions set forth the parameters of the present invention.

As used herein, the term "angiogenesis" refers to the process of formation and development of blood vessels.

The term "c-kit" refers to a protein on the surface of some cells that binds to stem cell factor (a substance that causes certain types of cells to grow). Altered forms of this receptor may be associated with some types of cancer.

The term "cardiac biomarkers" refers to enzymes, proteins and hormones associated with heart function, damage or failure that are used for diagnostic and prognostic purposes. Different biomarkers have different times that their levels rise, peak, and fall within the body, allowing them to be used not only to track the progress of a heart attack but to estimate when it began and to monitor for recurrence. Some of the tests are specific for the heart while others are also elevated with skeletal muscle damage Current cardiac biomarkers include, but are not limited to, CK (creatine phosphokinase or creatine kinase) and CK-MB (creatine kinase-myoglobin levels (to help distinguish between skeletal and heart muscle)), troponin (blood levels of troponin I or T will remain high for 1-2 weeks after a heart attack; troponin is not generally affected by damage to other muscles), myoglobin (to determine whether muscle, particularly heart muscle, has been injured), and BNP (brain natriuretic peptide) or NT-proBNP (N-terminal prohormone brain natriuretic peptide (to help diagnose heart failure and grade the severity of that heart failure).

The term "cardiac catheterization" refers to a procedure in which a catheter is passed through an artery to the heart, and into a coronary artery. This procedure produces angiograms (i.e., x-ray images) of the coronary arteries and the left ventricle, the heart's main pumping chamber, can be used to measure pressures in the pulmonary artery, and to monitor heart function.

The term "CD34$^+$ cells" as used herein refers to hematopoietic stem and progenitor cells derived from human bone marrow that "are positive for" i.e., "express", a hematopoietic stem cell antigen, at least a subpopulation of which express CXCR4, and that can migrate to areas of injury.

The term "CD38" refers to a protein marker present on macrophages, dendritic cells, and activated B and NK cells, which may mediate the adhesion between lymphocytes and endothelial cells.

The terms "CD45" and "common leukocyte antigen" refer to a protein tyrosine phosphatase (PTP) located in hematopoietic cells except erythrocytes and platelets.

The term "CD59" refers to a glycosylphosphatidylinositol (GPI)-linked membrane glycoprotein which protects human cells from complement-mediated lysis.

The term "chemotaxis" refers to the directed motion of a motile cell or part towards environmental conditions it deems attractive and/or away from surroundings it finds repellent.

The term "CXCR-4" as used herein refers to a G-protein-linked chemokine receptor.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNF and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "colony stimulating factor" refers to a cytokine responsible for controlling the production of white blood cells. Types include granulocyte colony stimulating factor (G-CSF), macrophage colony stimulating factor (M-CSF), and granulocyte macrophage colony stimulating factor (GM-CSF).

The term "hematopoietic stem cell" refers to a cell isolated from the blood or from the bone marrow that can renew itself, differentiate to a variety of specialized cells, mobilize out of the bone marrow into the circulating blood, and can undergo programmed cell death (apoptosis). In some embodiments of the present invention, hematopoietic stem cells derived from human subjects express at least one type of cell surface marker, including, but not limited to, CD34, CD38, HLA-DR, c-kit, CD59, Sca-1, Thy-1, and/or CXCR-4, or a combination thereof.

"HLA-DR" refers to a human class II histocompatibility antigen present on several cell types, including antigen-presenting cells, B cells, monocytes, macrophages, and activated T cells.

The term "interleukin" as used herein refers to a cytokine secreted by white blood cells as a means of communication with other white blood cells.

The terms "VEGF-1" or "vascular endothelial growth factor-1" are used interchangeably to refer to a cytokine that mediates numerous functions of endothelial cells including proliferation, migration, invasion, survival, and permeability. VEGF is critical for angiogenesis.

The term "chemokine" as used herein refers to a class of chemotactic cytokines that signal leukocytes to move in a specific direction. The term "chemotactic" refers to movement or orientation of a cell along a chemical concentration gradient either toward or away from a chemical stimulus.

The term "complete blood count" (CBC) refers to a laboratory test that provides detailed information about the amount and the quality of each of the blood cells types. It usually includes a measurement of each of the three major blood cells (red blood cells, white blood cells, and platelets) and a measure of the hemoglobin and hematocrit. "Hemoglobin" (HGB) refers to the number of grams of hemoglobin in a deciliter of blood (g/dL). Normal hemoglobin levels in healthy adult human subjects are about 14 g/dL to about 18 g/dL for men and about 12 g/dL to about 16 g/dL for women. As a rough guideline, hemoglobin generally should be about one-third the hematocrit. "Red Blood Cell Count" (RBC) refers to the total number of red blood cells in a quantity of blood. Normal ranges in human subjects are about 4.5 million cells/mm$^3$ to about 6.0 million cells/mm$^3$ for men and about 4.0 million cells/mm$^3$ to about 5.5 million cells/mm$^3$ for women. "White Blood Cell Count" (WBC) refers to the total number of white blood cells or leukocytes in a quantity of blood. Normal ranges in human subjects are about 4.3×103 cells/mm$^3$ to about 10.8×103 cells/mm$^3$. "Hematocrit" (HCT) refers to the proportion of red blood cells as a percentage of total blood volume. A normal hematocrit for human subjects is about 40% to about 55% for men and about 35% to about 45% for women.

The term "disease" or "disorder", as used herein, refers to an impairment of health or a condition of abnormal functioning. The term "syndrome," as used herein, refers to a pattern of symptoms indicative of some disease or condition. The term "condition", as used herein, refers to a variety of health states and is meant to include disorders or diseases caused by any underlying mechanism or disorder, injury, and the promotion of healthy tissues and organs.

As used herein, the term "inflammation" refers to a response to infection and injury in which cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue.

Regardless of the initiating agent, the physiologic changes accompanying acute inflammation encompass four main features: (1) vasodilation, which results in a net increase in blood flow, is one of the earliest s physical responses to acute tissue injury; (2) in response to inflammatory stimuli, endothelial cells lining the venules contract, widening the intracellular junctions to produce gaps, leading to increased vascular permeability which permits leakage of plasma proteins and blood cells out of blood vessels; (3) inflammation often is characterized by a strong infiltration of leukocytes at the site of inflammation, particularly neutrophils (polymorphonuclear cells). These cells promote tissue damage by releasing toxic substances at the vascular wall or in uninjured tissue; and (4) fever, produced by pyrogens released from leukocytes in response to specific stimuli.

During the inflammatory process, soluble inflammatory mediators of the inflammatory response work together with cellular components in a systemic fashion in the attempt to contain and eliminate the agents causing physical distress. The terms "inflammatory" or "immuno-inflammatory" as used herein with respect to mediators refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, proinflammatory cytokines, including, but not limited to, interleukin-1, interleukin-4, interleukin-6, interleukin-8, tumor necrosis factor (TNF), interferon-gamma, and interleukin 12.

The term "in-date" refers to the time interval between completion of acquiring from the subject a preparation comprising an enriched population of potent CD34+ cells from a subject under sterile conditions and initiating sterilely purifying potent CD34+ cells from the preparation. The term "out-date" refers to the time interval between completion of acquiring from the subject a preparation comprising an enriched population of potent CD34+ cells from a subject under sterile conditions and infusing the formulated pharmaceutical composition comprising a chemotactic hematopoietic cell product into the subject.

The terms "infuse" or "infusion" as used herein refer to the introduction of a fluid other than blood into a blood vessel of a subject, including humans, for therapeutic purposes.

The "infusion solution" of the present invention without autologous serum contains phosphate buffered saline (PBS) supplemented with 25 USP units/ml of heparin and 1% human serum albumin (HSA). In some embodiments, the infusion solution is supplemented with serum. In some embodiments, the serum is autologous.

The term "injury" refers to damage or harm caused to the structure or function of the body of a subject caused by an agent or force, which may be physical or chemical. The term "vascular injury" refers to injury to the vasculature (i.e., the vascular network, meaning the network of blood vessels or ducts that convey fluids, such as, without limitation, blood or lymph).

The term "macrophage" as used herein refers to a mononuclear, actively phagocytic cell arising from monocytic stem cells in the bone marrow. These cells are widely distributed in the body and vary in morphology and motility. Phagocytic activity is typically mediated by serum recognition factors, including certain immunoglobulins and components of the complement system, but also may be nonspecific. Macrophages also are involved in both the production of antibodies and in cell-mediated immune responses, particularly in presenting antigens to lymphocytes. They secrete a variety of immunoregulatory molecules.

The term "microbe" or "microorganism" are used interchangeably herein to refer to an organism too small to be seen clearly with the naked eye, including, but not limited to, microscopic bacteria, fungi (molds), algae, protozoa, and viruses.

The term "modulate" as used herein means to regulate, alter, adapt, or adjust to a certain measure or proportion.

The term "myocardial infarction" refers to death or permanent damage to heart muscle. Most heart attacks are caused by blockage of coronary arteries that interrupts flow of blood and oxygen to the heart muscle, leading to death of heart cells in that area. The damaged heart muscle loses its ability to contract, leaving the remaining heart muscle to compensate for the weakened area. The present invention includes steps related to evaluating the suitability of subjects for treatment according to the present invention by using tests to look at the size, shape, and function of the heart as it is beating, to detect changes to the rhythm of the heart, and to detect and evaluate damaged tissues and blocked arteries. Examples of such tests include, but are not limited to, electrocardiography, echocardiography, coronary angiography, and nuclear ventriculography. Cardiac biomarkers also are used to evaluate the suitability of subjects for treatment according to the present invention.

As used herein, the term "potent" or "potency" refers to the necessary biological activity of the chemotactic hematopoietic stem cell product of the present invention, i.e., potent cells of the present invention remain viable, are capable of mediated mobility, and are able to grow, i.e., to form hematopoietic colonies in an in vitro CFU assay.

The term "progenitor cell" as used herein refers to an immature cell in the bone marrow that can be isolated by growing suspensions of marrow cells in culture dishes with added growth factors. Progenitor cells mature into precursor cells that mature into blood cells. Progenitor cells are referred to as colony-forming units (CFU) or colony-forming cells (CFC). The specific lineage of a progenitor cell is indicated by a suffix, such as, but not limited to, CFU-E (erythrocytic), CFU-GM (granulocytic/macrophage), and CFU-GEMM (pluripotent hematopoietic progenitor).

The term "repair" as used herein as a noun refers to any correction, reinforcement, reconditioning, remedy, making up for, making sound, renewal, mending, patching, or the like that restores function. When used as a verb, it means to correct, to reinforce, to recondition, to remedy, to make up for, to make sound, to renew, to mend, to patch or to otherwise restore function. In some embodiments "repair" includes full repair and partial repair.

The term "Sca-1" or "stem cell antigen-1" refers to a surface protein component in a signaling pathway that affects the self-renewal ability of mesenchymal stem cells.

The term "stem cells" refers to undifferentiated cells having high proliferative potential with the ability to self-renew that can generate daughter cells that can undergo terminal differentiation into more than one distinct cell phenotype.

The term "stent" is used to refer to small tube used to prop open an artery. The stent is collapsed to a small diameter, put over a balloon catheter, inserted through a main artery in the groin (femoral artery) or arm (brachial artery) and threaded up to the narrowed/blocked section of the artery. When it reaches the right location, the balloon is inflated slightly to push any plaque out of the way and to expand the artery (balloon angioplasty). When the balloon is inflated, the stent expands, locks in place and forms a scaffold to hold the artery open. The stent stays in the artery permanently. In certain subjects, a stent reduces the renarrowing that occurs after balloon angioplasty or other procedures that use catheters. A stent also may help restore normal blood flow and keep an artery open if it has been torn or injured by the balloon catheter. Reclosure (restenosis) is a problem with the stent procedure. Drug-eluting stents are stents coated with drugs that are slowly released. These drugs may help keep the blood vessel from reclosing.

The term "subject" as used herein includes animal species of mammalian origin, including humans.

The term "Thy-1" refers to the Ig superfamily cell surface glycoprotein Thy-1 expressed on immune cells and neurons of rodents and humans, which is hypothesized to function in cell adhesion and signal transduction in T cell differentiation, proliferation, and apoptosis.

As used herein the term "treating" includes abrogating, substantially inhibiting, slowing or reversing the progression of a condition, substantially ameliorating clinical or aesthetical symptoms of a condition, substantially preventing the appearance of clinical or aesthetical symptoms of a condition, and protecting from harmful or annoying stimuli.

Compositions of the Present Invention

In one aspect of the present invention, the hematopoietic stem cells of the present invention can migrate, meaning that they can move from one place, location or area to another. In one embodiment, hematopoietic stem cell migration is driven by chemotaxis.

The present invention provides pharmaceutical compositions and methods for repair of injury caused by vascular insufficiency. The terms "formulation" and "composition" are used interchangeably herein to refer to a product of the present invention that comprises all active and inert ingredients. The term "active" refers to the ingredient, component or constituent of the compositions of the present invention responsible for the intended therapeutic effect. The terms "pharmaceutical formulation" or "pharmaceutical composition" as used herein refer to a formulation or composition that is employed to prevent, reduce in intensity, cure or otherwise treat a target condition or disease.

The pharmaceutical composition for repair of vascular injury of the present invention comprises a chemotactic hematopoietic stem cell product comprising an enriched population of CD34+ cells containing a subpopulation of cells having chemotactic activity. In some embodiments, this chemotactic activity is mediated by SDF-1, VEGF, and/or CXCR-4. According to one embodiment, the chemotactic hematopoeitic stem cell product is prepared by isolating or purifying CD34+ hematopoietic stem cells from bone marrow harvested from the subject. According to the present invention, the chemotactic hematopoietic stem cell product enriched for CD34+ cells contains at least about 70%, at least about 75%, at least about 80%, at least about 85%, at least about 90% or at least about 95% pure CD34+ cells. In another embodiment, at least about 70%, at least about 75%, at least about 80%, at least about 85%, at least about 90% or at least about 95% of the CD34+ cells are viable for at least about 24, at least about 48 hours, or at least about 72 hours following acquisition of the enriched population of CD34+ cells. In another embodiment, the CD34+ cells can form hematopoietic colonies in vitro for at least about 24, at least about 48 hours, or at least about 72 hours following acquisition of the enriched population of CD34+ cells.

CD34+ cells can be enriched/selected by any techniques known to the skilled artisan. For example, in some embodiments, the population of bone marrow cells comprising CD34+ cells is enriched for cells expressing CD34 cell antigen and CXCR4 cell antigen by fluorescence activated cell sorting (FACS). In some embodiments, CD34+ cells in the bone marrow are enriched/selected by positive or negative immunoseparation techniques. In some embodiments, isolation and/or purification of hematopoietic stem cells from the bone marrow is based on cell fractionation methods based on size and cell density, efflux of metabolic dyes, or resistance to cytotoxic agents. In one embodiment, for example, CD34+ cells in the bone marrow are enriched/selected using a monoclonal anti-CD34 antibody and an immunomagnetic separation technique.

The selected CD34+ cells can be identified, quantified and characterized by techniques known in the art. For example, in some embodiments, the percentage of CD34+ cells in the bone marrow and in the chemotactic hematopoietic stem cell product can be determined by FACS analysis. In another embodiment, CD34 protein expression is quantified by Western blot. The term "Western blot" refers to a method for identifying proteins in a complex mixture; proteins are separated electrophoretically in a gel medium; transferred from the gel to a protein binding sheet or membrane; and the sheet or membrane containing the separated proteins exposed to specific antibodies which bind to, locate, and enable visualization of protein(s) of interest. For example, monoclonal anti-CD34 antibody can be used to detect CD34 protein adhered to a membrane in situ.

In another embodiment, the expression of CD34 mRNA and DNA in the isolated CD34+ cells can be quantified. The term "Northern blot" as used herein refers to a technique in which RNA from a specimen is separated into its component parts on a gel by electrophoresis and transferred to a specifically modified paper support so that the mRNA is fixed in its electrophoretic positions. CD34 related sequences are identified using probes comprising a reporter molecule, such as, without limitation, a radioactive label. In another embodiment, the level of CD34 and/or CXCR4 expression is/are determined by quantitative or semi-quantitative PCR or reverse transcriptase PCR ("RT-PCR") techniques. The abbreviation "PCR" refers to polymerase chain reaction, which is a technique for amplifying the quantity of DNA, thus making the DNA easier to isolate, clone and sequence. See, e.g., U.S. Pat. Nos. 5,656,493, 5,333,675, 5,234,824, and 5,187,083, each of which is incorporated herein by reference.

In another embodiment, the selected CD34+ hematopoietic stem cells of the chemotactic hematopoietic stem cell product of the present invention contain a subpopulation of CD34+ cells having CXCR-4 mediated chemotactic activity. In a preferred embodiment, the hematopoietic stem cell product of the present invention comprises a minimum number of isolated CD34+ hematopoietic stem cells such that a subpopulation of at least $0.5 \times 10^6$ CD34+ cells having CXCR-4 mediated chemotactic activity is present. In another embodiment, at least about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, or 34% of the CXCR-4 mediated chemotactic activity of the CD34+ cells is retained for at least 24 hours, at least 48 hours, or at least 72 hours following acquisition of the enriched population of CD34+ cells. In another embodiment, at least an average of about 17% of the CXCR-4 mediated chemotactic activity of the CD34+ cells is retained for at least 24 hours, at least 48 hours, or at least 72 hours following acquisition of the enriched population of CD34+ cells. In another embodiment, the CD34+ cells in the chemotactic hematopoietic cell product retain at least about 2% of the CXCR-4 mediated chemotactic activity for at least 72 hours following acquisition of the enriched population of CD34+ cells.

The pharmaceutical composition of the present invention further comprises serum at a concentration of at least 10% by volume of the composition. In one embodiment, the serum is autologous. In another embodiment, the serum is a synthetic or recombinant serum. The minimum concentration of serum present in the composition is at least about 10%, 15%, 20%, 25%, 30%, 35%, 40%, 45%, 50%, 55%, 60%, 65%, or 70% expressed as ml/100 cc final volume of the composition. The maximum concentration of serum present in the composition of the present invention is about 70%, 65%, 60%, 55%, 50%, 45%, 40%, 35%, 30%, 25%, 20%, 15%, or 10% expressed as ml/100 cc final volume of the composition.

In some embodiments, the composition of the present invention may be formulated with an excipient, carrier or vehicle including, but not limited to, a solvent. The terms "excipient", "carrier", or "vehicle" as used herein refers to carrier materials suitable for formulation and administration of the Chemotactic hematopoietic stem cell product described herein. Carriers and vehicles useful herein include any such materials known in the art which are nontoxic and do not interact with other components. As used herein the phrase "pharmaceutically acceptable carrier" refers to any substantially non-toxic carrier useable for formulation and administration of the composition of the present invention in which the chemotactic hematopoietic stem cell product of the present invention will remain stable and bioavailable.

The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions of the present invention include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like. Such carrier solutions also can contain buffers, diluents and other suitable additives. The term "buffer" as used herein refers to a solution or liquid whose chemical makeup neutralizes acids or bases without a significant change in pH. Examples of buffers envisioned by the present invention include, but are not limited to, Dulbecco's phosphate buffered saline (PBS), Ringer's solution, 5% dextrose in water (D5W), normal/physiologic saline (0.9% NaCl). In some embodiments, the infusion solution is isotonic to subject tissues. In some embodiments, the infusion solution is hypertonic to subject tissues. Compositions of the present invention that are for parenteral administration can include pharmaceutically acceptable carriers such as sterile aqueous solutions, non-aqueous solutions in common solvents such as alcohols, or solutions in a liquid oil base.

In some embodiments, the carrier of the composition of the present invention may include a release agent such as sustained release or delayed release carrier. In such embodiments, the carrier can be any material capable of sustained or delayed release of the active to provide a more efficient administration, e.g., resulting in less frequent and/or decreased dosage of the composition, improve ease of handling, and extend or delay effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

The compositions of the present invention may be administered parenterally in the form of a sterile injectable aqueous or oleaginous suspension. The term "parenteral" or "parenterally" as used herein refers to introduction into the body by way of an injection (i.e., administration by injection), including, but not limited to, infusion techniques. The composition of the present invention comprising a chemotactic hematopoietic stem cell product is delivered to the subject by means of a balloon catheter adapted for delivery of the fluid compositions (i.e., compositions capable of flow) into a selected anatomical structure.

The sterile composition of the present invention may be a sterile solution or suspension in a nontoxic parenterally acceptable diluent or solvent. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it doesn't rapidly settle out. In everyday life, the most common suspensions are those of solids in liquid water. Among the acceptable vehicles and solvents that may be employed are water, Ringer's solution, and isotonic sodium chloride (saline) solution. In some embodiments, hypertonic solutions are employed. In addition, sterile, fixed oils are conventionally employed as a solvent or suspending medium. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran.

Additional compositions of the present invention can be readily prepared using technology which is known in the art such as described in Remington's Pharmaceutical Sciences, 18th or 19th editions, published by the Mack Publishing Company of Easton, Pa., which is incorporated herein by reference.

As used herein the terms "therapeutically effective," "vascular injury repairing amount", "vascular insufficiency repairing amount", or "pharmaceutically effective amount" refer to the amount of the compositions of the invention that result in a therapeutic or beneficial effect following its administration to a subject. The vascular insufficiency repairing, vascular injury repairing, therapeutic, or pharmaceutical effect can be curing, minimizing, preventing or ameliorating a disease or disorder, or may have any other vascular insufficiency-reducing, vascular injury-repairing, or pharmaceutical beneficial effect. The concentration of the substance is selected so as to exert its vascular insufficiency repairing, vascular injury repairing, therapeutic, or pharmaceutical effect, but low enough to avoid significant side effects within the scope and sound judgment of the physician. The effective amount of the composition may vary with the age and physical condition of the biological subject being treated, the severity of the condition, the duration of the treatment, the nature of concurrent therapy, the timing of the infusion, the specific compound, composition or other active ingredient employed, the particular carrier utilized, and like factors.

A skilled artisan can determine a pharmaceutically effective amount of the inventive compositions by determining the dose in a dosage unit (meaning unit of use) that elicits a given intensity of effect, hereinafter referred to as the "unit dose." The term "dose-intensity relationship" refers to the manner in which the intensity of effect in an individual recipient relates to dose. The intensity of effect generally designated is 50% of maximum intensity. The corresponding dose is called the 50% effective dose or individual ED50. The use of the term "individual" distinguishes the ED50 based on the intensity of effect as used herein from the median effective dose, also abbreviated ED50, determined from frequency of response data in a population. "Efficacy" as used herein refers to the property of the compositions of the present invention to achieve the desired response, and "maximum efficacy" refers to the maximum achievable effect. The amount of the chemotactic hematopoietic stem cell product in the pharmaceutical compositions of the present invention that will be effective in the treatment of a particular disorder or condition will depend on the nature of the disorder or condition, and can be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, New York, 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993). The precise dose to be employed in the formulations of the present invention also will depend on the route of administration and the seriousness of the disease or disorder, and should be decided according to the judgment of the practitioner and each subject's circumstances. It is envisioned that subjects may benefit from multiple administrations of the pharmaceutical composition of the present invention.

It is preferred that the pharmaceutical compositions according to the present invention contain a minimum number of CD34+ hematopoietic stem cells having a subpopulation of at least $0.5 \times 10^6$ CD34+ cells having CXCR-4 mediated chemotactic activity per dosage unit for parenteral administration at the physician's discretion.

In another aspect of the present invention, the pharmaceutical compositions of the present invention can further include one or more compatible active ingredients which are aimed at providing the composition with another pharmaceutical effect in addition to that provided by the isolated chemotactic hematopoietic stem cell product of the present invention. "Compatible" as used herein means that the active ingredients of such a composition are capable of being combined with each other in such a manner so that there is no interaction that would substantially reduce the efficacy of each active ingredient or the composition under ordinary use conditions. In some embodiments, the combination therapy comprises administering to a subject in need thereof a pharmaceutical composition comprising a chemotactic hematopoietic stem cell product of the present invention combined with an agent selected from the group consisting of an angiotensin converting enzyme (ACE) inhibitor, a beta-blocker, a diuretic, an anti-arrhythmic agent, an anti-anginal agent, a vasoactive agent or inotrope, an anticoagulant agent, a fibrinolytic agent, and a hypercholesterolemic agent.

In some embodiments, the composition of the present invention further comprises about 0.5% to about 5% albumin. In some embodiments, the minimum amount of albumin is about 0.5%, about 0.75%, about 01.0%, about 1.25%, about 1.5%, about 1.75%, about 2.0%, about 2.5%, about 2.75%, about 3.0%, about 3.5%, about 4.0%, about 4.5%, or about 5.0%, expressed as ml/100 cc volume of the composition. In some embodiments, the maximum amount of albumin in the compositions of the present invention is about 5.0%, about 4.75%, about 4.5%, about 4.25%, about 4.0%, about 3.75%, about 3.5%, about 3.25%, about 3.0%, about 2.75%, about 2.5%, about 2.25%, about 2.0%, about 1.75%, about 1.5%, about 1.25%, or about 1.0%, expressed as ml/100 cc volume of the composition. In some embodiments, the albumin is human albumin. In some embodiments the albumin is recombinant human albumin.

Methods of the Present Invention

In another aspect, the present invention provides a method of preparing the pharmaceutical composition comprising a chemotactic hematopoietic stem cell product for treating a subject in need thereof. The method comprises the steps of (1) acquiring a preparation comprising an enriched population of potent CD34+ cells from the subject under sterile conditions by a chemotactic cell acquisition process;

(2) sterilely purifying potent CD34+ cells containing a subpopulation of potent cells having chemotactic activity from the preparation;

(3) sterilely formulating the purified potent CD34+ cells to form the chemotactic hematopoietic stem cell product;

(4) sterilely formulating the chemotactic hematopoietic stem cell product containing a subpopulation of potent CD34+ cells having chemotactic activity to form a pharmaceutical composition;

(5) assessing sterility of the pharmaceutical composition;

(6) releasing the sterile pharmaceutical composition as eligible for infusion into the subject;

(7) loading a therapeutically effective amount of the pharmaceutical composition into an intravascular delivery apparatus; and (8) optionally transporting the delivery apparatus containing the therapeutically effective amount of the sterile pharmaceutical composition comprising the chemotactic hematopoietic stem cell product to a cardiac catheterization facility for infusion in to the subject.

In one embodiment, step (2) is initiated within about 12 hours to about 24 hours of completion of acquiring step (1). In another embodiment, releasing step (7) proceeds only if the sterile formulated cell product is to be infused into the subject within about 48 hours to about 72 hours of completion of acquiring step (1). In another embodiment, step (2) is initiated within about 12 hours to about 24 hours of completion of acquiring step (1), and releasing step (6) proceeds only if the sterile formulated cell product is to be infused into the subject within about 48 hours to about 72 hours of completion of acquiring step (1).

In one embodiment, step (5), i.e., the step of assessing sterility of the pharmaceutical composition further comprises the steps of (i) centrifuging the chemotactic hematopoietic stem cell product comprising potent CD34+ cells to form a cell pellet and a supernatant, the cell pellet comprising the potent CD34+ cells; (ii) sterilely removing the supernatant without disturbing the cell pellet; and (iii) analyzing whether the supernatant is contaminated by a microbe thereby determining the sterility of the cell pellet.

In one embodiment, in step (a), the chemotactic cell acquisition process is a mini-bone marrow harvest technique used to acquire a preparation comprising an enriched population of potent CD34+ cells from the bone marrow of the subject under sterile conditions. For the bone marrow harvest technique, step (a) of the method further comprises the steps: (i) preloading harvesting syringes with heparin prior to harvesting bone marrow from a subject; (ii) aspirating the bone marrow from a left posterior iliac crest and a right posterior iliac crest of the subject using the harvesting syringes and a mini-bone marrow harvest technique to form harvested bone marrow; and (iii) infusing the harvested bone marrow into a collecting bag. In one embodiment, the harvesting syringes in step (i) and the collecting bag in step (iii) contain a preservative free heparinized solution comprising 0.9% normal saline. The final concentration of heparin in the heparinized saline solution is about 20 units per ml to about 25 units per ml.

Optionally, in one embodiment of the method, the harvested bone marrow is transported to a processing facility different from the facility from which the bone marrow was harvested. In one embodiment, the method for transporting the harvested bone marrow to the processing facility comprises the steps (a) placing the harvested bone marrow in a collection bag; (b) placing the collection bag in a secondary bag; (c) placing the secondary bag containing the collection bag in a shipping container comprising an interior compartment containing frozen wet ice and at least one sheet of bubble wrap; (d) affixing a temperature tag monitor to the interior compartment of the shipping container; (e) sealing the shipping container; and (f) shipping the shipping container to the processing facility.

In another aspect, the present invention provides a method of treating injury due to vascular insufficiency in a subject in need thereof, the method comprising the steps: (a) evaluating whether the subject qualifies for therapy with the pharmaceutical composition of the present invention; (b) preparing the pharmaceutical composition comprising a chemotactic hematopoietic stem cell product; (c) loading the pharmaceutical composition into an intravascular delivery apparatus; (d) delivering a therapeutically effective amount of the pharmaceutical composition to the subject intravascularly (meaning inside a blood vessel); and (e) monitoring the subject's cardiac function.

According to one embodiment of the present invention, the subject in need thereof is a revascularized myocardial infarction patient. The term "revascularized" as used in this embodiment refers to the successful placement of a stent. Clinical evaluations, for example, of coronary insufficiency using non-laboratory tests, cardiac catheterization, measurement of inflammatory cytokines, and measurement of cardiac biomarkers can be used to determine the appropriate time to administer the pharmaceutical compositions in accordance with the methods of the present invention. In some embodiments, detection of peak inflammatory cytokine cascade production enables the administration to be tailored at the window most crucial for the particular subject. In some embodiments, peak inflammatory cytokine cascade production is determined by the measuring the levels of the appropriate cytokine(s) in the plasma and or urine. In other embodiments, the level(s) of the appropriate cytokine(s) is/are measured immunochemically, for example, by a sandwich enzyme immunoassay, by enzyme-linked immunosorbent assays (ELISA) or by multiplex bead kits.

According to one embodiment, the composition is administered to the subject after an inflammatory cytokine cascade production peaks. In some embodiments, the composition is administered to the revascularized myocardial infarction patient about 5 days to about 14 days post-infarction. The minimum time in which to administer the composition to the revascularized myocardial infarction patient is about 5, 6, 7, 8, 9, 10, 11, 12, 13, or 14 days. The maximum time in which to administer the composition is about 14, 12, 11, 10, 9, 8, 7, 6, or 5 days.

The intravascular delivery apparatus used to deliver the pharmaceutical composition of the present invention to a subject in need thereof comprises an infusion syringe, a flushing syringe, a four-way stopcock, and a balloon catheter. In one embodiment, the intravascular delivery comprises (a) an infusion device attached to a sterile four-way stopcock containing the pharmaceutical composition comprising the chemotactic hematopoietic stem cell product; (b) a flushing device attached to the sterile four-way stopcock, the flushing device containing a flushing solution, and (c) a catheter attached to the delivery apparatus by the sterile four-way stopcock. According to one embodiment, the infusion device is a syringe made of any suitable material. The body and handle of suitable four way stopcocks may be made of the same or a different material. Examples of suitable four-way stopcocks includes, without limitation, a stopcock having a polycarbonate body/polycarbonate handle, a stopcock having a polyethylene body/polyethylene handle, a stopcock having a polycarbonate body/polyethylene handle, or a disposable stopcock. In another embodiment, a device is further attached to the stopcock to regulate the pressure exerted on the delivered solution. In some embodiments an integral flush device or syringe is attached to the stopcock. In one embodiment, the catheter is a balloon catheter. The term "balloon catheter" refers to a type of "soft" thin flexible tube having an inflatable "balloon" at its tip which is used during a catheterization procedure to enlarge a narrow opening or passage within the body. The deflated balloon catheter is positioned, inflated to perform the necessary procedure, and deflated again to be removed.

The viability and potential efficacy of the chemotactic hematopoietic stem cell product of the present invention comprising potent CD34+ cells depends on the cells maintaining their potency as they pass through a catheter. The catheter used in the methods of the present invention has an internal diameter of at least 0.36 mm. Any type of catheter having an internal diameter of at least 0.36 mm may be effective in delivering the pharmaceutical compositions of the present invention.

For example, a flow control catheter, which slows drainage of blood through the coronary artery vasculature allows the cells time to transit through the blood vessel wall and into the tissue.

In some embodiments, the catheter is a balloon catheter. For example, without limitation, the following balloon dilatation catheters available from Cordis, Boston Scientific, Medtronic and Guidant having an internal diameter of about 0.36 mm have been validated (see Table 1).

TABLE 1

Balloon catheter validated for infusion of selected CD34+ cells through the IRA

| Manufacturer | Name and Model No. | Balloon Dimensions | Lumen Internal Diameter |
|---|---|---|---|
| Cordis | Raptor OTW 579-130 | 15 mm × 3.0 mm | 0.36 mm (0.14 in.) |
| Boston Scientific | OTW Maverick 20620-1530 | 15 mm × 3.0 mm | 0.36 mm (0.14 in.) |
| Medtronic | OTW Sprinter SPR 3015W | 15 mm × 3.0 mm | 0.36 mm (0.14 in.) |
| Guidant | Voyager OTW 1009443-15 | 15 mm × 3.0 mm | 0.36 mm (0.14 in.) |

In addition, catheters have been described having a fluid delivery port adjacent the balloon such that the balloon may be inflated against a vessel wall to isolate the delivery site from hemodynamics opposite the balloon from the port, which may be located distally of the balloon. Additionally, balloon catheters have been disclosed having lumens ending in side ports disposed proximally to the balloon catheter; these balloon catheters generally may be referred to as "balloon/delivery" catheters, although particular references may use different descriptors. See, e.g., U.S. Pat. No. 5,415,636 to Forman, incorporated by reference.

In some embodiments, the method of treating or repairing a vascular injury comprises administering the composition via balloon catheterization into an infarcted artery. In some embodiments, following angioplasty a delivery balloon catheter is inserted via a femoral artery into a desired coronary artery, such as the left anterior descending coronary artery. Some medical conditions may require both a balloon catheter and a fluid delivery catheter to facilitate treatment.

In some embodiments, a catheter is used to directly inject cells into the myocardium.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges also is encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a", "and", and "the" include plural referents unless the context clearly dictates otherwise. All technical and scientific terms used herein have the same meaning.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be confirmed independently.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Selection of Eligible Subjects

Subjects/patients presenting with symptoms and clinical findings suggestive of a myocardial infarction will receive emergency diagnostic and clinical management according to institutional guidelines. If a transmural (meaning through the wall) myocardial infarction is confirmed, the time of first symptoms and the time of successful stent placement will be recorded. Revascularized subjects will receive appropriate medical management to reduce ventricular wall stresses according to institutional guidelines. The term "revascularized" as used in this embodiment, refers to the successful placement of a stent.

All types of stents, including drug-eluting stents (e.g., paclitaxel or sirolimus) are acceptable for use in the revascularization of the infarct related artery ("IRA"). Previous studies employing balloon catheters to infuse cell products have reported no limits for reference vessel diameter for the placement of the stent. Since this study is designed to distribute the cell product into the IRA circulation, and in an attempt to limit the potential for damage to very small vessels, the present invention requires that stents be placed prior to infusion of the chemotactic hematopoietic stem cell product of the present invention.

Stent-related drug effects occur predominantly at the site of contact of the stent with the vessel wall. Consequent to balloon dilatation, there is limited blood flow across the stent during cell infusion, and therefore no significant adverse drug-mediated effect on the $CD34^+$ cells in the chemotactic hematopoietic stem cell product is expected. Moreover, prior clinical studies have shown that by 96 hours after drug-eluting stent placement, whole blood levels of either paclitaxel or sirolimus are below the limits of detection. Therefore, tissue levels in the myocardial sites to which the infused $CD34^+$ cells having CXCR-4-mediated chemotactic activity are intended to migrate are expected to be inconsequential. See Sousa, J. et al., Circulation 107: 2274-79, 2383-89 (2003).

During revascularization, a subject's cardiac function and perfusion will be assessed by standard methods. Relevant measures of cardiac function following a myocardial infarction include assessment of global and regional ejection fraction, ventricular volumes, resting and stress perfusion, segmented wall motion and infarct size.

Echocardiography, radionuclide scanning (e.g., Multiple Gated Acquisition scan (MUGA), a nuclear scan that evaluates the pumping function of the ventricles, chambers and how the heart contracts) and left ventriculography all are readily available and accurate measures of left ventricular ejection fraction ("LVEF"). Echocardiography has been utilized to determine end-systolic and end-diastolic volumes by using the biplane area length method. The left ventricular wall motion score index ("WMSI") is calculated by dividing the left ventricle into segments and then grading systolic wall motion and thickening by a semi-quantitative score index as follows: 1=normal or hyperkinesia; 2=hypokinesia; 3=akinesia; and 4=dyskinesia. As used herein, the term "hyperkinesias" refers to excessive movement or muscular activity; the term "hypokinesia" refers to diminished or slow movement or muscular activity; the term "akinesia" refers to the absence or loss of movement or muscle activity; and the term "dyskinesia" refers to abnormal movement or muscular activity. The WMSI then is obtained by dividing the sum of the segment scores by the number of segments assessed. See Schiller, N. B. et al., J. Am. Soc'y Echocardiogr. 2: 358-67 (1989). Newer echocardiographic modalities allow for assessment of regional ejection fraction, myocardial perfusion, and post stress wall abnormalities.

Other measures of cardiac function in the post-infarct period include assessment of the stroke volume index and velocity of circumferential fiber shortening. Strauer, et al., Circulation 106: 1913-18 (2002). Assessment of repair of infarcted myocardium also has included evaluation of peri-infarct region perfusion using thallium scintigraphy. Id. Most recently, magnetic resonance imaging (MRI) appears to be the most useful tool for assessing cardiac function and viability (infarct size) in this setting. See Yin, A, et al., Blood 90: 5002-5012 (1997).

The day after successful stenting, subjects will be assessed for study eligibility and, if appropriate, will be offered informed consent to participate in the study. Subjects exhibiting symptoms for no more than three (3) days prior to successful stent placement will be assessed, prior to discharge, for study eligibility. Subjects found to meet eligibility criteria (see infra) will be offered informed consent to participate.

Consented subjects will have a study entry echocardiogram no sooner than 96 hours after stent placement. Subjects are eligible to proceed on study if the LVEF is less than or equal to 50% on echocardiography and a segmental ventricular wall abnormality is observed in the IRA. Eligible subjects immediately can complete baseline cardiac function and perfusion assessment.

Specifically, baseline cardiac function includes: transthoracic echocardiography at rest and with low dose dobutamine to assess cardiac function including ejection fraction, end systolic and diastolic volumes, and wall motion score index and viability. Myocardial contrast echocardiography will be used to assess segment wall motion and myocardial blood flow at the tissue level. Myocardial strain rates also will be assessed. Perfusion will be assessed using a routine Tc-99m Sestamibi radionuclide scan at rest and after intravenous adenosine. Regional and global wall motion, infarct size, and left ventricular ("LV") volumes will be measured using MRI. Subjects will receive Gadolinium contrast during scanning. MRI scan will use the breath holding technique. Steady state precession imaging to obtain global and regional LV function will be performed as will Gadolinium imaging. Left ventricular end systolic and diastolic volumes, LVEF, LV end diastolic dimension, wall thickness in systole and diastole of the infarcted region, and infarct size will be reported using the AHA/AVV 17-segment model with transmural extent of the infarct reported as <25%, 26%-50%, 51%-75% and >76%. A core review laboratory will assess MRI with the interpreter blinded to the study cohort.

To be selected for this study, subjects must meet all of the following clinical criteria ("inclusion criteria"):
Age: 18-75 years;
Acute ST segment elevation myocardial infarction meeting ACC/AHA criteria, with symptoms of chest pain within 3 days of admission. Criteria include (ST elevation>1 mm in limb leads or 2 mm in two or more precordial leads and increased levels of troponin, creatine kinase MB (CPK MB) or both), New York Heart Association (NYHA) heart failure class (to be recorded) of I, II or III;
Eligible for percutaneous coronary intervention (PCI);
Eligible for MRI;
Eligible for Single Proton Emission Computed Tomography (SPECT) imaging;
Echocardiograph lab conclusion of ability to adequately assess cardiac parameters after review of admission echocardiography;
Study entry echocardiogram (96 to 144 hours {i.e., about 4 days to about 6 days} after stent placement), LVEF less than or equal to 50% on echocardiography, and segmental ventricular wall abnormality in the IRA circulation by echocardiography after reperfusion;
Subject must be able to provide informed written consent and must be willing to participate in all required study follow-up assessments;
Subjects must have a hemoglobin content (Hgb) >10 grams/dL, white blood cell count (WBC) >3500 cells/mm$^3$, a platelet count >100,000 cells/mm$^3$ and a international normalized ratio (INR, a blood coagulation test) <2.0 the day before the bone marrow collection;
Subjects must have a serum creatinine <2.5, total bilirubin <2.0 within 7 days of the bone marrow collection;
IRA and target lesion must be clearly identifiable when disease is present in more than one vessel;
Successful reperfusion and intracoronary stent placement, with Thrombolysis In Myocardial Infarction (TIMI) 2 or 3 flow and IRA with <20% stenosis after revascularization;
Subjects must be deemed eligible to receive conscious sedation, mini-bone marrow harvest, and second catheterization for Chemotactic hematopoietic stem cell product infusion;
The type of stent used and time and date inserted must be recorded;
Drug eluting stents should be limited to paclitaxel or sirolimus types;
Included subjects must have an expected survival of at least one year and must not have multiple vessel disease after revascularization, or be expected to require intervention within 6 months of study entry.

Subjects who satisfy any one of the following criteria do not qualify for, and will be excluded from, the study ("exclusion criteria"):
Subjects who are not candidates for percutaneous intervention, conscious sedation, MRI, SPECT imaging or mini-bone marrow harvest;
History of sustained chest pain unrelieved by nitrates, occurring 4 or more days before revascularization;
Subjects who fail to re-perfuse the infarct related coronary artery or to have successful stent placement;
Echocardiography lab conclusion after admission echocardiography review that study is not adequate to assess cardiac parameters;
Subjects presenting with cardiogenic shock (systolic pressure <80 on vasopressors or intra aortic counterpulsation);
Subjects with a side branch of the target lesion >2 mm and with ostial narrowing >50% diameter stenosis after revascularization;
Subjects unable to receive aspirin, clopidogrel or ticlopidine;
Subjects receiving warfarin must have an INR less than or equal to 2; the term INR refers to INR International Normalized Ratio, which is a system established by the World Health Organization (WHO) and the International Committee on Thrombosis and Hemostasis for reporting the results of blood coagulation (clotting) tests;
Subjects with severe aortic stenosis;
Subjects with severe immunodeficiency states (e.g., AIDS);
Subjects with cirrhosis requiring active medical management;
Subjects with malignancy requiring active treatment (except basal cell skin cancer);
Subjects with documented active alcohol and/or other substance abuse;
Females of child bearing potential unless a pregnancy test is negative within 7 days of the mini-bone marrow harvest;
Subjects with ejection fractions greater than 50% on study entry echocardiogram (96 to 144 hours after stent placement);
Subjects with less than three months of planned anti-platelet therapy post index procedure;
Subjects with multi vessel disease after revascularization requiring subsequent planned intervention during the next 6 months;

Subjects with participation in an ongoing investigational trial;

Subjects with active bacterial infection requiring systemic antibiotics.

Baseline assessments of cardiac function and cardiac perfusion will be obtained one day prior to the planned mini-bone marrow harvest and infusion of the chemotactic hematopoietic stem cell product (see infra). A mini-bone marrow harvest ("MMH") will be performed the day following baseline assessment of cardiac function and cardiac perfusion.

Example 2

Cardiac Catheterization

Sterile Preparation and Draping

The subject will be brought into the Cardiac Catheterization Laboratory after the investigator has obtained an informed consent. The subject will receive a sterile preparation and draping in the Cardiac Catheterization Laboratory.

Cardiac Catheterization

Vascular access will be obtained by standard technique using right or left groin. A sheath will be placed in the femoral artery or the right or left brachial artery. Coronary arteriographic examination will be performed by obtaining standard views of both right and left coronary arteries. Multiple views will be obtained to identify the previously stented infarct related artery. All subjects will receive standard medications during the catheterization procedure in accordance with routine practice.

Example 3

Acquisition Process for Acquiring Chemotactic Hematopoietic Stem Cell Product that can then be Enriched for CD34+ Cells While it is contemplated that any acquisition process appropriate for acquiring the chemotactic hematopoietic stem cell product comprising potent CD34+ cells is within the scope of the present invention, the following example illustrates one such process referred to herein as a mini-bone marrow harvest technique.

Preparation of Harvesting Syringes

Prior to the bone marrow harvest, forty 10 cc syringes loaded with about 2-ml of a preservative free heparinized saline solution (about 100 units/ml to about 125 units/ml, APP Cat. No. 42592B or equivalent) will be prepared under sterile conditions. Heparin will be injected via a sterile port into each of two 100-ml bags of sterile 0.9% normal saline solution ("Normal Saline", Hospira Cat. No. 7983-09 or equivalent) following removal of 10 cc to 12.5 cc of normal saline from each bag, resulting in a final heparin concentration of about 100 units/ml (U/ml) to about 125 units/ml (U/ml). 2-ml of the preservative free heparin solution (about 100 U/ml to about 125 U/ml) will be loaded under sterile conditions into each of the forty 10 cc syringes, which then are capped and placed into a sterile bag for transport to the harvesting site.

Subjects will be prepared for bone marrow harvest after written informed consent is obtained as detailed in Example 1. Conscious sedation will be provided using standard institutional procedures and guidelines. Bone marrow harvest will be conducted under sterile conditions. The term "sterile conditions" as used herein includes proper scrubbing and gowning with a sterile mask and gloves worn by the harvesting attending and assistant. The harvesting procedure can be performed outside of an operating room as follows: after sterile prepping and draping, each iliac crest should be anaesthetized with a 1% lidocaine solution using a minimum of 10-ml for each crest. The area of anesthesia should be a circular area no less than 10 cm in diameter. The harvesting needle is inserted until the iliac crest is punctured. The cap and stylet is removed and 2-ml of marrow is harvested into the 10-ml harvesting syringe containing 2-ml of the heparin solution. The syringe then is removed and placed on the sterile field. After re-inserting the stylet, the harvesting needle is advanced slightly and then rotated 90°. The stylet is then removed and an additional 2-ml of marrow is drawn into the harvesting syringe retrieved from the sterile field. This procedure is repeated two more times until the harvesting syringe contains 8-ml of marrow for a total of 10-ml of heparinized marrow at a final heparin concentration of about 20 U/ml to about 25 U/ml. Finally the full harvesting syringe is handed to the harvesting assistant and shaken and infused in the sterile collecting bag as described below. The harvesting physician then takes the other harvesting needle that had been flushed previously with the heparin solution and repeats this process.

The full harvesting syringe is infused in the sterile collecting bag as follows. The harvesting assistant is handed the full harvesting syringe and empties it in the 500-ml collecting bag though the sterile adaptor attached to the bag. Then the harvesting needle is flushed with the heparin solution in the flushing syringe and retuned to the sterile field.

The harvesting process is repeated on one iliac crest until about 19 syringes have been collected and emptied in the collecting bag. The same process is repeated on the other iliac crest until another about 19 syringes have been filled. A total of thirty-eight 8 ml aspirations from both iliac crest (ideally 19 from each iliac crest) will result in 302-ml of bone marrow harvested in a final volume of 380 ml at a heparin concentration of about 20 U/ml to about 25 U/ml.

The collecting bag is sealed by tying off the connecting tube three times and then clamped distal to the ties. The bag is appropriately labeled "Human Bone Marrow Collection" and the results of the harvesting procedure, including final volume collected and any procedure related complication, are recorded on the Mayo Clinical Risk Score (MCRS) case report form. The completed label is affixed to the bone marrow bag. The bag then is placed in a sterile carrying bag to be transported to the processing facility.

Example 4

Preparation of the Bone Marrow Product for Transportation

In one embodiment, the harvested bone marrow is transported to the processing facility as follows. When the clinical site is prepared to ship the bone marrow preparation, 24-hour notice will be provided to the processing facility. The processing laboratory will make shipping arrangements at the earliest possible time for pickup for same day delivery to the processing laboratory. Immediately after the bone marrow is collected, the bone marrow product will be placed in the supplied shipping container. The shipping container contains two small blocks of frozen wet ice on the bottom and a sheet of bubble wrap on top of the wet ice. The bone marrow product is placed into a secondary bag and the secondary bag is placed on top of the bubble wrap. A temperature tag monitor (a sensor used to monitor the internal temperature) is affixed to the interior of the box. Another layer of bubble wrap then is placed on top of the product before the shipping container is sealed off.

Example 5

Selection of CD34+ Cells from the Harvested Bone Marrow Product $CD34^+$ cells will be isolated from the harvested bone marrow product. In one embodiment, $CD34^+$ cells will be isolated using the anti-CD34 monoclonal antibody (Mab), Dynabeads® M-450 Sheep anti-Mouse IgG, and PR34+™ Stem Cell Releasing Agent components of the Isolex 300i Magnetic Cell Selection System (Baxter Healthcare Corp. Cat. No. 4R9734) as described in U.S. Pat. Nos. 5,536,475, 5,035,994, 5,130,144, 4,965,204, 5,968,753, 6,017,719, 6,251,295, 5,980,887, 6,676,937, U.S. Published Application No. 2003/0232050, and the Isolex 300i Package Insert, each of which is incorporated herein by reference. This operating system has been adapted for isolation of $CD34^+$ cells from bone marrow according to the present invention.

Upon arrival at the processing laboratory, the harvested bone marrow product (in the collecting bag) is inspected immediately and the bag checked for any leakage. The collection should be free flowing with no apparent clumps and should not be hemolyzed. The collection will not be used if the integrity of the bag has been breached in any way.

The bone marrow product should be processed within about 12 hours to about 24 hours of inspection. A 300-ml or 400-ml transfer pack container is obtained, and a plasma transfer set is attached to the sampling port of the container. The bone marrow product is transferred from the collecting bag to the transfer pack container. The pooled bone marrow collection product is mixed thoroughly by inverting the container twenty (20) times.

The pooled bone marrow collection product then is sampled for analysis. In one embodiment, a total volume of 2.0 ml of the product is removed and aliquoted as follows: 0.3 ml is used for a duplicate run of Complete Blood Count (CBC) using a hematology analyzer; 0.2-ml is dispensed into a 75×100-mm glass tube for the detection of Gram positive and Gram negative bacteria by Gram Stain (Gram Stain Kit, VWR, Cat. NO. BB231401); as a sterility check, 0.6-ml is dispensed into a Tryptic Soy Broth (TSB) (VWR, Cat. No. 29446-184) bottle for aerobic bacteria growth assay, 0.6-ml is dispensed into a Fluid Thioglycollate Media (FTM) (VWR Cat. # 29446-138) bottle for anaerobic bacteria growth assay, and 0.3-ml is used in flow analysis for $CD34^+$ cell enumeration and cell viability.

The collection is weighed on an electronic scale, and the appropriate tare weight of the collection bag recorded. The relationship of the volume of the bone marrow product to the weight of the product can be expressed as Volume (ml)=[Weight (gm) of product−Tare weight of bag (gm)]÷1.06 (gm/ml)    (Formula 1)

The number of Total Nucleated Cells (TNC) in the bone marrow product is calculated using the white blood cell (WBC) count obtained from the CBC according to the following relationship:

TNC=WBC/μl×1000×Product volume (ml)    (Formula 2)

The number of CD34+ cells in the bone marrow product is calculated from the following relationship:

Total $CD34^+$ cells in the bone marrow product=Number of $CD34^+$ cell/μl×1,000×Product volume (ml)    (Formula 3)

The Red Blood Cell (RBC) volume of the bone marrow collection product is calculated from the following relationship:

RBC volume (ml)=Product volume (ml)×Hematocrit (%)/100    (Formula 4),

If the collection contains more than 20 ml of RBC, red blood cell depletion is required. RBCs are depleted by centrifugation. Centrifugation at 1000×g for 20 minutes at ambient temperature is performed to separate the buffy coat from the RBCs. The term "buffy coat" refers to a thin grayish white fraction of a blood sample that contains most of the white blood cells (leukocytes). Immediately after centrifugation, a 60 ml syringe is connected to the bottom of the centrifugation bag and the RBCs are removed. More than one syringe may be needed to collect all the packed RBC. The RBC depleted bone marrow product then is washed to remove fat contents.

A 1-ml syringe is used to remove 0.3-ml of the RBC-depleted bone marrow cell product through the transfer set attached to the product bag and a CBC performed. The TNC of the RBC depleted bone marrow product is determined from the relationship:

Total TNC of the RBC depleted product=WBC/μl of RBC depleted product×1000×180-ml    (Formula 5)

The TNC recovery of the RBC depleted product, which must be at least 80% of the original product count, is calculated from the relationship:

TNC recovery=TNC of the RBC depleted product÷TNC of the unprocessed product×100%    (Formula 6)

The total RBC volume is calculated as described supra; the RBC volume in the RBC depleted product should be less than <20-ml.

In one embodiment according to the present invention, the Isolex 300i system is used to process the RBC-depleted product or the bone marrow product whose RBC volume is <20 ml according to the following processing steps:

(i) The bone marrow is washed automatically to remove platelets;

(ii) CD34 positive (CD34+) cells are labeled specifically for selection by incubation with the Isolex 300i CD34 monoclonal antibody (Mab);

(iii) Unbound reagent is removed by washing the cell suspension with buffer solution;

(iv) Sensitized CD34+ cells (meaning CD34+ cells labeled with CD34 Mab) are captured by Dynabeads M-450 Sheep anti-Mouse IgG;

(v) A selection column is used to separate the magnetically-labeled Dynabeads having captured CD34+ cells from unwanted cells, which are washed through the selection column and collected in the Negative Fraction Bag; and (vi) PR34+ Stem Cell Releasing Agent releases CD34+ cells from the column, and the CD34+ cells are collected in the End Product Bag. The system performs several washing steps, disposing of most of the liquid into the Buffer Waste Bag.

The Isolex® selected CD34+ fraction is assayed as follows to determine WBC and CD34+ cell yields. The volume of the CD34 Positive Fraction is determined by mixing the cells in the End Product Bag; the bag is gently massaged by hand to ensure even cell distribution. A transfer set is inserted into the sampling port of the End Product Bag and a 60-ml syringe attached. The cell suspension is withdrawn into the syringe (maximum 50-ml at a time) in order to measure the total volume.

A 3-ml or 5-ml syringe is used to remove a 2.0-ml sample from the End Product Bag through the transfer set for quality control testing. The aliquoted volumes of the samples and the analyses performed on those samples are as previously described, i.e., CBC: 0.3-ml; Gram stain: 0.3-ml; CD34+ cell enumeration and cell viability: 0.2-ml.

The total TNC of the CD34 Positive Fraction is calculated from the relationship:

Total TNC of the Positive Fraction=WBC/μl of the Positive Fraction×1000×Volume of the Positive Fraction (Formula 7)

The TNC recovery of the Positive Fraction, which must be less than 5% of the original product count, is calculated from the following relationship:

TNC recovery=Total TNC of the Positive Fraction÷Total TNC of the unprocessed product× 100% (Formula 8)

The total number of viable CD34+ cells in the Positive Fraction is determined from the following relationship:

Total CD34+ cells in the Positive Fraction=Number of CD34+ cells/μl of the final product×1,000×Final product volume (ml) (Formula 9)

The CD34+ cell recovery of the Positive Fraction is calculated from the following relationship:

CD34+ cell recovery=Total CD34+ cells of the Positive Fraction÷Total CD34+ cells of the unprocessed product×100% (Formula 10).

Example 6

Preparation of Selected CD34+ Cells for Transfusion

Samples of the chemotactic hematopoietic stem cell product will be removed to be assayed for WBC count, by flow cytometry (for CD34+ cell enumeration and viability), Gram stain, and sterility.

CD34+ cells are characterized by flow cytometric analysis featuring $CD34^{bright}$ and $CD45^{dim}$ fluorescence by double labeling with anti-CD34 and anti-CD45 antibodies (Beckman Coulter, PN IM3630). CD34+ cells and $CD45^+$ cell viability is determined by excluding the dying cells which take up the intercalating DNA dye 7-aminoactinomycin D (7AAD). See Brocklebank A M, Sparrow R L. Cytometry. 2001; 46:254-261 (2001); Barnett D, et al. Br. J Haematol. 106:1059-1062 (1999); Sutherland, et al., J Hematotherapy 5:213-226 (1996), and U.S. Pat. Nos. 4,520,110; 4,859,582; 5,055,556; European Patent No. 76.695; Canadian Patent No. 1,179,942 (PE, APC); U.S. Pat. No. 4,876,190 (PerCP); U.S. Pat. Nos. 5,268,486; 5,486,616; 5,569,587; 5,569,766; 5,627,027 (Cy); U.S. Pat. Nos. 4,714,680; 4,965,204; 5,035,994 (CD34); U.S. Pat. No. 5,776,709 (Lyse/no-wash method); U.S. Pat. Nos. 5,723,218 and 5,187,288 (TruCOUNT Tubes), the contents of each of which is incorporated by reference herein in its entirety.

Any flow cytometer or an equivalent device can be used for conducting analysis of CD34+ cell enumeration and viability. In one embodiment, the processing laboratory employs a BD FACSCalibur™ flow cytometer and BD FACSComp™ software is used for instrument setup and monitoring. A template and a panel of legend labels are preinstalled for acquisition and analysis. Prior to use, the reagents, namely CD45FITC/CD34PE, Stem-Count Fluorospheres, Concentrated Ammonium Chloride Lysing Solution, and 7AAD Viability Dye, are brought to ambient temperature. CD34+ cell controls are run as a positive control to affirm that the instrument is set up for analyzing CD34+ cells, and the results are compared with the manufacturer's pre-determined CD34 percent range.

The unprocessed bone marrow product and Isolex processed chemotactic hematopoietic stem cell products may be analyzed by many different procedures. In one embodiment, or example, immediately upon receiving the sample, if the WBC count of the sample is greater than $2\times10^7$ cells per ml, the sample is diluted with Sheath fluid to achieve a cell count of about $2\times10^7$ WBC per ml. 100 μl of the diluted product is aliquoted into two 15×100 mm tubes. Using a micropipetter, 201 of CD45FITC/CD34 PE and 7-AAD viability dye reagent are added into each tube and the samples gently vortexed. The tubes are covered with aluminum foil and left at ambient temperature for 15 to 20 minutes. RBCs are lysed by adding 1.5 ml of 1× Lysing Solution to each tube, vortexing gently. The tubes are incubated for ten minutes at ambient temperature, protected from light. The samples are stored at about 2° C.-about 8° C. (i.e., on an ice bath) protected from light until data acquisition is performed. Data acquisition must be performed within one hour of adding the lysing buffer. Before data acquisition, Stem-Count Fluorospheres are resuspended by end-over-end rotation (10 times). 100 μl of Fluorospheres is added to each tube and gently vortexed taking care not to generate air bubbles. The absolute count of CD34+ cells in the product is calculated from the relationship:

$$\text{Number of viable } CD34+ \text{ cells per μl of product} = \frac{LCD34 \times FAC}{F} \quad \text{(Formula 11)}$$

where LCD34 is the averaged number of events for Live $CD34^+$/All CD $45^+$; "FAC" is Fluorospheres Assayed Concentration; and F is the averaged number of Fluorosphere singlets counted.

The volume of CD34+ Positive Fraction is calculated to obtain the number of CD34+ cells required for the required dosing. The Required Positive Fraction Volume (ml) is defined as:

The Requested CD34+ cell dosage÷(Total CD34+ cells per μl in the Positive Fraction×1,000). (Formula 12)

An appropriate number of cells is dispensed into a 50 ml conical tube and centrifuged at 500×g for 10 minutes. The supernatant is removed using a 30 ml serological pipette and disposed of as waste while exercising care not to disperse the cell pellets at the bottom of the tubes during this process. The infusion solution (20 ml) is added into the CD34+ Cell Positive Fraction tube and the cells dispersed using a 10 ml serological pipette by repeat pipetting. The resuspended cells are centrifuged for 10 minutes at 500 g. A 30 ml serological pipette is used (without disturbing the cell pellet) to transfer the supernatant/infusion solution into a 50 ml conical tube with a label "Positive Fraction Supernatant" affixed. The tube containing the supernatant is vortexed to homogenize the solution. A 10 ml serological pipette is used to transfer 10 ml of the homogenized supernatant back to the CD34+ Cell Positive Fraction tube. The remaining 10 ml of suspension in the Supernatant tube will be used for sterility testing (5 ml each into a TSB (Trypticase Soy Broth) bottle and an FTM (Fluid Thioglycollate) bottle). The cells in the CD34+ Cell Positive Fraction are resuspended by slowly withdrawing and aspirating through a blunt end needle affixed to a 10 ml syringe (Infusion Syringe) several times. The cell suspension is withdrawn into the syringe, any air bubbles are aspirated off, and the blunt end needle removed. The infusion syringe is attached to the injection port of a 4-way stopcock.

The chemotactic hematopoietic stem cell product of the present invention will be released for infusion only if it meets the following criteria:
- CD34+ cell purity of at least about 70%, 75%, 80%, 85%, 90% or 95%;
- A negative Gram stain result for the selected positive fraction;
- Endotoxin Levels: less than about 0.5 endotoxin units/ml;
- Viable CD34+ cell yield of the "Chemotactic hematopoietic stem cell product" meets the required dosing as per the treatment cohort;
- CD34+ cells are at least about 70%, 75%, 80%, 85%, 90% or 95% viable by 7-AAD;
- USP sterility result for "Positive Fraction Supernatant": negative (14 days later); and
- Bone marrow CD34$^+$ cell selection was initiated within about 12 hours to about 24 hours of completion of bone marrow harvest.

Sterility assessment on the stem cell product including gram staining and endotoxin will be performed prior to product release for infusion. USP sterility (bacterial and fungal) culture will be performed and the results will be reported to the principal investigator. In the event of a positive USP sterility result, the subject and attending physician on call will be notified immediately, provided with identification and sensitivity of the organism when available, and documentation of appropriate anti-microbial treatment and treatment outcome will be recorded by the investigative site and the sponsor.

After meeting these release criteria, the chemotactic hematopoietic stem cell product will be released for infusion and packaged for transportation to the catheterization facility. A sample also will be sent for in vitro testing. Product will be released only if CD34+ cell selection is initiated within 12 hours to about 24 hours of completion of bone marrow harvest and only if it is to be infused within about 48 hours to about 72 hours of completion of bone marrow harvest.

Example 7

Formulation of the Chemotactic Hematopoietic Stem Cell Product Comprising CD34+ Cells The chemotactic hematopoietic stem cell product is formulated in 10-ml of saline (0.9% Sodium Chloride, Injection, USP, Hospira, Cat# 7983-09) supplemented with 1% HSA (Human Albumin USP, Alpha, Cat. # 521303) ("Infusion Solution") and at least 10% autologous serum. In addition, there may be some trace amount of materials (quantities not determined) in the Chemotactic hematopoietic stem cell product that are used and left over during the product processing. These materials include: Dulbecco's Phosphate Buffered Saline-Ca$^{++}$, Mg++ Free (D-PBS) (Baxter, Cat. # EDR9865), Sodium Citrate (Baxter/Fenwal, Cat. # 4B7867), Hetastarch (Abbott Laboratories, Cat. # 0074-7248-03), IVIg (Gammagard® Immune Globulin Intravenous, Baxter, Cat. # 060384) and the reagents in the Isolex® 300i Stem Cell Reagent Kit (Baxter, Cat. # 4R9734) including anti-CD34 monoclonal antibody, stem cell releasing agent and Sheep anti-mouse magnetic beads.

Example 8

Transporting Chemotactic Hematopoietic Stem Cell Product to the Catheterization Facility The chemotactic hematopoietic stem cell product that meets the release criteria will be loaded into a sterile 10 cc syringe in a Class 100 biological safety cabinet located within a controlled aseptic environment, e.g., at minimum, a Class 100,000 cell processing facility; class 10,000 is preferable, but not required. The chemotactic hematopoietic stem cell product will be suspended in 10-ml PBS supplemented with HSA and the container labeled in accordance with release criteria. There are to be four dosing cohorts consisting of five subjects each in each cohort. The first will receive about $5 \times 10^6$ CD34$^+$ cells, the second about $10 \times 10^6$ CD34$^+$ cells, the third about $20 \times 10^6$ CD34$^+$ cells and the fourth about $30 \times 10^6$ CD34$^+$ cells. Subjects in cohorts 2-4 with inadequate CD34$^+$ cell quantities to meet the assigned cohort dose will be added to a prior cohort at the greatest possible CD34$^+$ cell dose. The loaded infusion syringe will be attached to a four-way stopcock along with a flushing syringe, capped and have safety guards applied to prevent leakage. The delivery apparatus will be sealed in a double sterile bag and placed in a secure transportation box for transportation to the cardiac catheterization facility. Following release of the chemotactic hematopoietic stem cell product and cohort assignment, the chemotactic hematopoietic stem cell product will be shipped to the catheterization site for direct infarct-related artery infusion ("intravascular administration").

Example 9

Intra-Coronary Infusion of Chemotactic Hematopoietic Stem Cell Product

Upon notification from the cell processing facility that the chemotactic hematopoietic stem cell product has been released for infusion (see supra), the subject/patient will be scheduled to arrive at the catheterization facility at a time to coincide with the arrival of the chemotactic hematopoietic stem cell product.

Cardiac enzymes (brain natriuretic peptide (BNP), troponin and CPK MB), complete blood counts, a full chemistry panel (renal and liver function test) and an EKG will be performed just prior to chemotactic hematopoietic stem cell product infusion. Clinical assessment of the stage of heart failure according to the New York Heart Association's (NYHA) functional classification system will be recorded.

Upon receipt of the chemotactic hematopoietic stem cell product and final quality assurance release (by facsimile) for infusion, the subject will undergo cardiac catheterization as detailed above. Coronary arteriography will be performed to assess for patency (meaning openness, freedom from blockage) of the infarct related artery and Thrombolysis in Myocardial Infarction (TIMI) angiographic flow. A balloon catheter over a wire will be placed in the stented segment of the infarct related artery. Any appropriate balloon dilatation catheter having an internal diameter of at least about 0.36 mm compatible with the chemotactic hematopoietic stem cell product infusion can be used. After positioning, the balloon wire will be removed. The chemotactic hematopoietic stem cell product delivery apparatus will be removed from the transportation case.

The delivery apparatus will be in a sterile bag and have safety blocks attached to the infusion syringe (containing the chemotactic hematopoietic stem cell product) and the flushing syringe. The apparatus consists of the infusion syringe (containing 10 ml of the chemotactic hematopoietic stem cell product) and the flushing syringe (containing 6 ml of flushing solution) wherein both are attached to a sterile four-way stopcock. The entire delivery apparatus should be shaken gently to resuspend the CD34$^+$ cells in the infusion solution. The flushing syringe is used to eliminate all air bubbles in the apparatus (to prevent air emboli) and the delivery apparatus then attached to the balloon dilatation catheter via the stopcock.

Delivery of the chemotactic hematopoietic stem cell product to the subject by infusion will proceed as follows. First, with the stopcock open between the flushing syringe (6 ml solution) and the central lumen of the balloon catheter, 1 ml of flushing solution should be infused (after removal of the guard) into the central lumen of the catheter over 15 seconds. Second, the balloon should be inflated at two atmospheres of pressure within the stent to avoid damage to the coronary artery endothelium and then the stopcock valve adjusted to allow infusion of the chemotactic hematopoietic stem cell product distal to the inflated balloon (after removal of the guard). With the balloon inflated, about 3 cc to about 4 cc from the infusion syringe will be infused by hand over a period of about 30 seconds to about 45 seconds (to be timed and documented). The balloon will remain inflated to allow adhesion of the $CD34^+$ cells and to prevent back flow for a total of about 2 minutes to about 3 minutes (including the time for infusion). In between infusions, the balloon will remain deflated for 3 minutes to allow restoration of blood flow (reperfusion). It is expected that 3 infusions will be required to empty the infusion syringe. Third, upon completion of infusing the chemotactic hematopoietic stem cell product and with the balloon deflated, the valve on the stopcock will be adjusted to allow filling of the infusion syringe from the flushing syringe. Finally, with the balloon inflated (about 2 minutes to about 3 minutes), the 4 ml of flushing solution now in the infusion syringe will be infused over a period of about 30 seconds to about 45 seconds to dislodge any residual $CD34^+$ cells from the syringe and catheter into the IRA circulation. The catheter then is removed.

An infusion related ischemia (inadequate blood flow) assessment will be performed during the first 24 hours after chemotactic hematopoietic stem cell product infusion. An EKG at about 12 hours and at about 24 hours and analytical chemistry of cardiac enzymes (BNP, troponin and CPK MB) about every 8 hours for about 24 hours will be obtained. Arrhythmia assessment (24 hour Holter monitor) will be performed immediately post-chemotactic hematopoietic stem cell product infusion. Routine transthoracic echocardiography to evaluate global and regional left ventricular function will be performed prior to the subjects discharge after chemotactic hematopoietic stem cell product infusion.

All subjects will be provided with digital thermometers and a log book to record twice daily temperatures for 30 days post infusion of the chemotactic hematopoietic stem cell product. Subjects will be instructed to notify the investigator site immediately for temperatures recorded above 100.5° F. Rapid follow-up with appropriate cultures and radiographic assessments will be performed according to routine clinical standards. Documented bacterial infections will be reported to the IRB and the FDA.

Additional follow-up visits for safety assessments will include visits at 1 week and 2 weeks after product administration. Visit assessments will include a comprehensive medical history and physical examination, EKG, complete blood counts, full chemistry panel (renal and liver function test), and measure of serum cardiac markers (BNP, troponin and CPK MB). Clinical assessment of NYHA functional class will be recorded on week 1 and 2.

At 1 week post infusion, routine transthoracic echocardiography is to be performed.

At 4 weeks post chemotactic hematopoietic stem cell product infusion, an EKG and cardiac enzymes (BNP, troponin and CPK MB) will be obtained. Routine transthoracic echocardiography to evaluate global and regional left ventricular function also is to be performed. A 24 Holter monitor will be used to assess for arrhythmias. Clinical assessment of NYHA functional class will be recorded. Treadmill exercise testing using a symptom limiting Bruce protocol will be performed as well.

At about 3 months and about 6 months post chemotactic hematopoietic stem cell product infusion, a 24 hour Halter monitor will be performed. Clinical assessment of NYHA functional class will be recorded. At about 6 months post chemotactic hematopoietic stem cell product infusion, a symptom limited treadmill exercise testing using the Bruce protocol will be recorded.

A safety assessment at about 12 months post chemotactic hematopoietic stem cell product infusion will include a comprehensive medical history and physical examination, EKG, complete blood counts, full chemistry panel (renal and liver function test), and measure of serum cardiac markers (BNP, troponin and CPK MB). Routine transthoracic echocardiography to evaluate global and regional left ventricular function also is to be performed. A 24 hour Holter monitor will be performed. Clinical assessment of NYHA functional class will be recorded.

Statistical Analysis

A paired design, where each subject serves as his or her own control, will be used in some embodiments. Differences between before and after treatment, per subject, will be analyzed for each of the four numeric cardiac functions (i.e., myocardial contractility; end systolic volume, end diastolic volume; and perfusion). Linear regression analysis will be used to assess the significance of increased dosing levels. The null hypothesis is that the slope of the regression line (dosing level serving as the independent variable and the "after" minus the "before" difference serving as the dependant variable) is equal to zero. The power of rejecting a false null hypothesis is 0.68 at the 0.05 alpha level of significance for a high correlation of 0.5 between dosing and improvement in cardiac function. The 95% confidence interval about the slope of the regression line will be used to assess the medical significance of the increase in dosing level. If the slope of the regression line is not significantly different from zero but the intercept of the regression line is different from zero, then all treatment groups will be combined and a paired t-test will be performed to assess the overall treatment effectiveness. The null hypothesis is that the mean of the differences is equal to zero. A Wilcoxon signed-ranks test also will be performed as an additional test to determine the treatment effectiveness. This test is more powerful (rejecting a false null hypothesis) than a t-test if the observations are not normally distributed. The power of the t-test is 0.79 for rejecting a false null hypothesis at the alpha level of 0.05 and the treatment having a medium size effect (an effect large enough to be discernable by the naked eye). The medical significance of the treatment effect size will be determined by computing a 95% confidence interval about the mean of the differences (the true mean of the differences will lay in this interval in 95% of tested samples).

To assess improvement in perfusion, logistic regression will be used with dosing level as the independent variable and perfusion change (1=yes, 0=no) as the dependant variable. Odds ratios of the four dosing levels will be computed separately with $5.0 \times 10^6$ cells serving as the index group.

A binomial test will be used to assess the significance of CD34+ cell dosing on perfusion. It is expected that there will be no spontaneous improvement in a perfusion defect if present on the baseline perfusion scan. Therefore, any clinically significant improvement in a perfusion defect when assessed at 6 months and compared to baseline will be considered a treatment effect.

A concurrent group (non-treated controls) meeting eligibility but not receiving CD34+ cells will be evaluated similar to the treated group and assessed for significant improvement in cardiac function/perfusion. Each study site will alternate accrual of treated and non-treated controls. A coin flip will be used to determine the initial (treated or non-treated) subject sequence at each site. Comparison of outcomes between treated and non-treated groups will be made. The core lab will be blinded regarding treatment or no-treatment.

An assessment will be performed to determine if a correlation exists between clinical outcome and cell content (CD34+) and/or in vitro colony growth (CFU-GM, CFU-GEMM, BFU-E), CXCR-4 mobility, and CXCR-4 and/or VEGF surface antigen expression.

A total of 20 subjects will receive the chemotactic hematopoietic cell product of the present invention. There will be four dose cohorts (about $5 \times 10^6$, about $10 \times 10^6$, about $20 \times 10^6$, and about $30 \times 10^6$ CD34+ cells). If the chemotactic hematopoietic stem cell product content in any subject is not sufficient for the assigned cohort, that subject will be reassigned to a prior cohort at the greatest possible dose. Subjects having fewer than $5 \times 10^6$ CD34+ cells available for infusion will be removed from study, will not undergo repeat catheterization and will not be counted as part of the 20-subject study group. In addition, if the chemotactic hematopoietic cell product of the present invention does not meet release criteria, the subject will not receive the cell product and will not be counted as a study candidate to be replaced by the next subject. In any cohort dosing group, if a subject experiences an acute (meaning immediate to about 7 days post infusion) unexpected toxicity considered to (probably) be a result of the cell product infusion, dose escalation will be halted and 3 additional subjects will be accrued to that dose level. If no other unexpected toxicity is observed, then dose escalation will resume, however the total of 20 subjects will not be exceeded. If another toxicity occurs at that dose level, then all subsequent subjects will be accrued to the next lower dose level.

The chemotactic hematopoietic stem cell product of the present invention will not be administered to any subject in the higher dose cohort until all the subjects from the prior dose cohort have completed their follow-up assessments two weeks after product administration.

Example 10

Experimental Results of Preliminary Studies

A series of preliminary preclinical studies have been performed in an attempt to accomplish the following goals:

(1) Optimize the manufacturing process for the Mini bone-Marrow Harvest (MMH);

(2) Evaluate the stability of the inbound MMH product and the outbound hematopoietic cell product.

(3) Evaluate the internal diameter allowance and safety of the catheters;

(4) Evaluate the compatibility of the cell product with the catheters intended to be used in the study; and (5) Evaluate the suitability of using the supernatant of the final hematopoietic cell product to represent the final hematopoietic cell product for stability testing.

Study 1: Optimizing the Manufacturing Process for the Mini Bone-Marrow Harvest (MMH);

The effect of key manufacturing variables on the yield of viable CD34 cells from representative bone marrow products was evaluated. A total of six (6) volunteer donors over the age of 45 (based on a range of 45-57) and three under 30 years of age (based a range of 21-28) agreed to donate an average of 45 ml (based on a range of 31 ml-54 ml) bone marrow and provided written Informed Consent for the procedure. The marrow aspiration technique employed was identical to that to be performed for the clinical scale MMH (see Example 3, supra). As shown in Table 2, the cell counts of nucleated cell (NC) and CD34+ cells of Mini bone-Marrow Harvest ("MMH") derived cells collected from volunteer donors appeared to be age related.

TABLE 2

Effect of donor age on nucleated cell yield of the MMH.

| | Over 45 (45-57) | | | Under 30 (23-28) | | |
|---|---|---|---|---|---|---|
| Donor | Volume of MMH (ml) | Viability (%) | CD34 cells ($10^5$ per ml) | Volume of MMH (ml) | Viability (%) | CD34 cells ($10^5$ per ml) |
| 1 | 31.30 | 83.85 | 1.27 | 48.00 | 96.90 | 7.98 |
| 2 | 43.50 | 97.42 | 3.89 | 50.60 | 96.28 | 11.60 |
| 3 | 51.50 | 85.74 | 1.37 | 39.90 | 87.17 | 5.99 |
| 4 | 47.50 | 80.95 | 1.76 | — | — | — |
| 5 | 53.70 | 98.21 | 5.58 | — | — | — |
| 6 | 44.90 | 96.36 | 4.48 | — | — | — |
| Avg. | 45.40 | 90.42 | 3.06 | 46.17 | 93.45 | 8.52 |

The average cell count of the bone marrow products from older donors (N=6) was $28.4 \times 10^6$ (based on a range of $15.8 \times 10^6$-$49.5 \times 10^6$) nucleated cells per ml ["NC/ml"], with an average viability, as determined by 7-AAD dye exclusion and flow cytometry, of 90.42% (based on a range of 80.95%-98.21%) and CD34+ content of $3.06 \times 10^5$/ml (based on a range of $1.27 \times 10^5$/ml -$5.58 \times 10^5$/ml). In the younger subject group (N=3), the average cell count collected from marrow aspiration was $46.2 \times 10^6$ NC/ml (based on a range of $39.9 \times 10^6$ NC/ml-$50.6 \times 10^6$ NC/ml), with an average 7-AAD viability of 93.5% (based on a range of 87.17%-96.90%) and total CD34+ content of $8.5 \times 10^5$/ml (based on a range of $5.99 \times 10^5$ CD34+ cells/ml-$11.60 \times 10^5$ CD34+ cells/ml).

Red Cell Depletion and CD34 Selection

TABLE 3

CD34+ cell recovery after RBC depletion of
MMH from older age group (4557) donors.

| | Donor | | | | | |
|---|---|---|---|---|---|---|
| | 1 | 2 | 3 | 4 | 5 | Average |
| Method of RBC depletion | Hetastarch | Buffy coat | Buffy coat | Buffy coat | Buffy coat | — |
| CD34+ cell % in MMH: Pre-RBC depletion | 1.09 | 1.64 | 1.63 | 1.45 | 1.99 | 1.58 |
| CD34+ cell % in MMH: Post-RBC depletion | 1.33 | 1.55 | 1.51 | 1.61 | 1.84 | 1.57 |
| CD34+ cell recovery post RBC depletion (%) | 65.68 | 92.36 | 80.66 | 78.79 | 81.67 | 79.83 |

As shown in Table 3, following red cell depletion of the MMH-derived bone marrow products collected from the older donors, an average of 79.83% (based on a range of 65.68%-92.36%) of the CD34 cells from the initial MMH was recovered. There was no significant difference between the initial CD34 cell purity (1.58%, based on a range of 1.09%-1.99%) and that following red cell depletion (1.57%, based on a range of 1.33%-1.84%).

TABLE 4

CD34+ cell recovery, purity, CXCR-4 migratory activity, viability
and hematopoietic CFU growth immediately after Isolex processing
of MMH from older age group (age 45-age 57) donors.

| | Donor | | | | | |
|---|---|---|---|---|---|---|
| | 1 | 2 | 3 | 4 | 5 | Average |
| Storage time (hours) at 4° C.-8° C. | 0 | 0 | 0 | 12 | 10.50 | — |
| CD34+ cell recovery (%) | 32.36 | 29.09 | 15.31 | 43.60 | 40.20 | 32.11 |
| CD34+ cell purity (%} | 76.76 | 73.64 | 71.66 | 72.52 | 72.01 | 73.32 |
| CD34+ cell viability | 98.49 | 93.80 | 97.38 | 98.28 | 98.39 | 97.27 |
| CD34+ cell CXCR-4 migratory activity (%) | 22.10 | 2.60 | 22.00 | 19.90 | 19.70 | 17.26 |
| Hematopoietic CFU/100 CF34+ cells cultured | 27.5 | 25.0 | 18.9 | 17.0 | 21.00 | 21.9 |

As shown in Table 4, following CD34 selection using the Isolex system, which includes immunomagnetic Dynabeads® and anti-CD34 MAb, we recovered an average of 32.11% (based on a range of 15.31%-43.60%) of the CD34 cells with an average purity of 73.32% (based on a range of 71.66%-73.64%) and an average viability of 97.27% (based on a range of 93.80%-98.49%). In addition, these CD34+ cells displayed an average of 17.26% (based on a range of 2.60%-22.10%) CXCR-4 migratory ability immediately after selection and were capable of generating hematopoietic colonies (21.89 colonies/100 CD34+ cells plated (based on a range of 17.0 colonies/100 CD34+ cells plated-27.5 colonies/100 CD34+ cells plated) in MethoCult culture.

Study 2: Evaluation of the Stability of the Inbound Mini-Bone Marrow Harvest and of the Outbound Chemotactic Hematopoietic Cell Product:

A series of experiments, using healthy volunteers, was performed in order to evaluate the stability of the inbound MMH and of the outbound chemotactic hematopoietic stem cell product of the present invention. Assessment of the functional viability of the inbound and outbound products was evaluated by cell viability (7-AAD), SDF-1/CXCR-4 mediated CD34+ cell migration, and the ability to form hematopoietic colonies in methylcellulose (CFU colony forming ability).

To evaluate the inbound product stability for shipping and logistic purposes and for coordination with clinical schedules, MMH products were stored at 4° C. to 8° C. as indicated. To evaluate the outbound product stability for shipping and logistic purposes, the chemotactic hematopoietic stem cell product comprising isolated CD34+ cells enriched following MMH was stored at 4° C. to 8° C. as indicated.

In preliminary studies, cells either were processed immediately or maintained at 4-8° C. for 12 hours prior to processing to evaluate the impact of shipping and logistic duration on the manufacture a suitable cell product for infusion. Despite the duration of storage prior to processing (inbound product expiration), the results did not vary significantly (data not shown).

In another series of experiments, cells were stored at about 4° C. to about 8° C. for 12 hours and about 24 hours prior to reassessment to simulate products infused at about 36 hours and at about 48 hours, respectively, following MMH.

TABLE 5

CD34+ cell viability, growth and CXCR-4 migratory
activity 13-13.5 hours after Isolex processing of MMH.

| | Donor | | |
|---|---|---|---|
| | 1 | 2 | Average |
| CD34+ cell viability (%) | 97.59 | 96.90 | 97.24 |
| CD34+ cell CXCR-4 migratory activity (%) | 7.70 | 7.50 | 7.60 |
| Hematopoietic CFU/100 CD34+ cells cultured | 18.00 | 25.00 | 21.5 |

As shown in Table 5, the isolated CD+34 cells of the chemotactic hematopoietic stem cell product had an average viability of 97.24% (based on a range of 96.90%-97.59%) and average CXCR-4-mediated migratory capacity of 7.60% (based on a range of 7.50%-7.70%). As shown in Table 6, after storage for an average of 26.3 hours (based on a range of 26.0 h-26.5 h), these cells had an average viability of 96.81% (based on a range of 96.39%-97.22%) and an average CXCR-4-mediated migratory capacity of 4.75% (based on a range of 4.50%-5.00%). Further, the cells still maintained their ability to generate hematopoietic colonies in vitro.

TABLE 6

CD34+ cell viability, growth and CXCR-4 migratory activity
26.0-26.5 hours after Isolex processing of MMH.

| | Donor | | |
|---|---|---|---|
| | 1 | 2 | Average |
| CD34+ cell viability (%) | 97.22 | 96.39 | 96.81 |
| CD34+ cell CXCR-4 migratory activity (%) | 4.50 | 5.00 | 4.75 |
| Hematopoietic CFU/100 CD34+ cells cultured | 28.00 | 14.00 | 21.00 |

Thus, an average of 13.3 hours (based on a range of 13.0 h-13.5 h) after CD34+ cell selection, representing 26.0-26.5 hr post-MMH, the CD34+ cell population had an average viability of 97.24% (based on a range of 96.90%-97.59%), with average CXCR-4 mediated migratory capacity of 7.60% (based on a range of 7.50%-7.70%). At an average of 26.3 hours (based on a range of 26.0 h-26.5 h) following MMH, the average viability of the cells was 96.81% (based on a range of 96.39%-97.2%) and maintained an average CXCR-4-mediated migratory capacity of 4.75% (based on a range of 4.50%-5.00%).

Formulation of the composition of the present invention comprising this product occurred an average of 8 hours (8.63±1.80 N=4) hours after MMH collection, and infusion occurred within 24 hours of MMH.

TABLE 7

CD34+ cell viability as a function of time after MMH: 12-hour in-dating and 48 hour outdating (all time points measured from completion of MMH.)

| Time (h) after MMH (SD) | CD34+ cell viability (%) | | | | Average (SD) |
|---|---|---|---|---|---|
| | A | B | C | D | |
|  | 98.22 | 97.13 | 97.60 | 99.00 | 97.99 (0.29) |
| 24 | 95.32 | 97.76 | — | — | 96.54 (1.73) |
| 33 | 91.92 | 96.32 | 95.90 | 80.00 | 91.04 (7.62) |

In a subsequent experiment, four (4) MMH products (A-D) were collected and stored at 4° C. for an average of 12.8 hours (based on a range of 12.5 h-13.0 h) before the CD34+ cells were isolated by the Isolex procedure. This group, representing the "12 hour in-date" group (meaning that the product was formulated within the in-date time of about 12 hours), was evaluated for functional viability out-date at "24 hours" (22.9 h±1.63, N=4), "33 hours" (33.38±1.11, N=2), and "48 hours" (48.33±0.82, N=4) post MMH harvest. The data, summarized in Tables 7-9, demonstrate that following MMH, the chemotactic hematopoietic stem cell product comprising enriched CD34+ cells maintains 1) high viability (>90.0% average viability, Table 7), 2) 76.85% (±21.66) of their SDF-1VEGF/CXCR-4 mediated migratory ability (Table 8), and 3) their ability to form hematopoietic colonies in vitro (Table 9), respectively.

Table 8 shows SDF-1/VEGF/CXCR-4 mediated CD34+ cell migration (% migrating CD34+ cells as a function of time after MMH: 12-hour in-dating and 48-hour outdating (all time points measured from completion of MMH). For the purposes of determining the impact of time post-MMH on the migratory ability of the CD34+ cells, time point "X" was considered the reference point, as this was determined to represent the earliest time point following MMH at which cells reasonably could be expected to be returned to the subject in a finished formulation. The remaining migratory activity at the following time points (Y=33 hours, Z=48 hours) was calculated as percent migratory ability remaining following the 24 hour (X) time point.

TABLE 8

SDF-1/VEGF/CXCR-4 mediated CD34+ cell migration (% migrating CD34+ cells as a function of time after MMH: 12-hour in-dating and 48-hour outdating (all time points measured from completion of MMH).

| Time (h) after MMH | Migrating CD34+ cells (%) | | | | Average (SD) |
|---|---|---|---|---|---|
| | A | B | C | D | |
| 24 (X) | 20.00 | 18.50 | 21.50 | 36.00 | 24 (8.09) |
| % Remaining | 100.00 | 100.00 | 100.00 | 100.00 | 100.00 (0) |
| 33 (Y) | 21.80 | 10.50 | — | — | 16.15 (7.99) |

TABLE 8-continued

SDF-1/VEGF/CXCR-4 mediated CD34+ cell migration (% migrating CD34+ cells as a function of time after MMH: 12-hour in-dating and 48-hour outdating (all time points measured from completion of MMH).

| Time (h) after MMH | Migrating CD34+ cells (%) | | | | Average (SD) |
|---|---|---|---|---|---|
| | A | B | C | D | |
| *% Remaining | 109.00 | 56.76 | — | — | 82.88 (36.94) |
| 48 (Z) | 8.80 | 17.00 | 17.50 | 31.00 | 18.58 (9.19) |
| @% Remaining | 44.00 | 91.89 | 81.40 | 86.00 | 75.85 (21.66) |

*= (Y ÷ X) × 100%
@= (Z ÷ X) × 100%

Table 9 shows the number of colony forming units (CFU) per 100 viable CD34+ cells plated as a function of time after MMH: 12-our in-dating and 48 hour-out-dating (all time points measured from completion of MMH.

TABLE 9

| Time (h) after MMH | # of CFU per 100 viable CD34+ cells plated | | | | Average (SD) |
|---|---|---|---|---|---|
| | A | B | C | D | |
| 24 | 13.00 | 30.00 | 37.00 | 39.00 | 29.75 (11.81) |
| 33 | 12.00 | 34.00 | — | — | 23.00 (15.56) |
| 48 | 15.00 | 30.00 | 20.00 | 8.00 | 28.25 (14.57) |

In an attempt to extend both the in-date and out-date stability parameters for the chemotactic hematopoietic stem cell product of the present invention comprising CD34+ cells from 12-hours (in-date) and from 48-hours (out-date) (12/48), respectively, to 24-hours (in-date) and 72-hours (outdate) (24/72), respectively, CD34 cells were purified about 12 hours after MMH harvest (12 hour in-date) and about 24 hours after MMH harvest (24 hour in-date) and analyzed for functional viability at about 48 hours and at about 72 hours total time from MMH to time of testing/anticipated infusion (48 hour out-date and 72 hour out-date, respectively). Specifically, the functional viability characteristics of two MMH/chemotactic hematopoietic stem cell products of the present invention were evaluated at 48 hours and 72 hours. The resulting data were further compared to the same indices derived at the previous 12/48 time points (Tables 7-9).

Tables 10-12 show that at 33 hours (based on 32.5±0.71, N=2), 48 hours (based on one data point at 49 hours), and at 72 hours (based on 72.5 h±0.71, N=2), the isolated CD34+ cells of the chemotactic hematopoietic stem cell product of the present invention maintain 1) over 90% viability (Table 10), 2) 102.19±32.69% of their SDF-11VEGF/CXCR-4 mediated migratory ability (Table 11), and 3) their ability to generate hematopoietic colonies in vitro (Table 12).

TABLE 10

CD34+ cell viability as a function of time after MMH: 24-h in-dating and 72-h outdating (all time points measured from completion of MMH)

| Time (h) after MMH | CD34+ cell viability (%) | | Average (SD) |
|---|---|---|---|
| | A | B | |
| 33 | 98.00 | 99.00 | 98.50 (0.71) |
| 48 | — | 97.00 | 97.00 (—) |
| 72 | 91.00 | 97.00 | 94.00 (4.24) |

TABLE 11

SDF-1/VEGF/CXCR-4 mediated CD34+ cell migration (% population of migrated CD34+ cells as a function of time after MMH): 24-h in-dating and 72-h outdating (all time points measured from completion of MMH):

| Time (h) after MMH (SD) | Migrating CD34+ cells (%) | | Average (range) |
|---|---|---|---|
| | A | B | |
| 33 | 8.20 | 14.05 | 11.13 (2.93) |
| % Remaining | 100.00 | 100.00 | 100.00 (0.00) |
| 48 | — | 18.61 | 18.61 (—) |
| % Remaining | — | 132.46 | 132.46 (—) |
| 72 | 5.70 | 18.95 | 12.33 (6.63) |
| % Remaining | 69.51 | 134.88 | 102.19 (32.69) |

The % remaining ratios in Table 11 were determined as in table 8 above.

TABLE 12

Number of CFU per 100 viable CD34+ cells plated as a function of time after MMH: 24-h in-dating and 72-h outdating (all time points measured from completion of MMH)

| Time (h) after MMH (SD) | # of CFU per 100 viable CD34+ cellsplated | | Average (range) |
|---|---|---|---|
| | A | B | |
| 33 | 26.00 | 28.50 | 22.25 (1.25) |
| 48 | — | 16.80 | 16.80 (—) |
| 72 | 14.50 | 27.50 | 21.00 (6.5) |

Further evaluation of the functional viability parameters of the chemotactic hematopoietic stem cell product comprising isolated CD34+ cells of the present invention ("clinical product") at 8 hours (8.6 h±1.80, N=4), 12 hours (12.87 h±1.92, N=4), 32 hours (one time point at 33.5 h), 48 hours (47.50 h±2.5, N=2), and 72 hours (71.5 h±0.50, N=2) after MMH shows that after 72 hours, the product retains its 1) viability (Table 13), 2) SDF-1/VEGF/CXCR-4 mediated migratory ability (Table 14) and 3) ability to form hematopoietic colonies in vitro (Table 15), equivalent to the 24-hour time point.

TABLE 13

Clinical Product Experience: CD34+ cell viability as a function of time after MMH.

| Time (h) after MMH | CD34+ cell viability (%) | | | | Average (SD) |
|---|---|---|---|---|---|
| | A | B | C | D | |
| 8 | 98.30 | 99.08 | 90.00 | 96.45 | 95.96 (4.12) |
| 12 | 98.89 | 96.96 | 99.00 | 99.43 | 98.57 (1.10) |
| 33 | — | 93.42 | — | — | 93.42 |
| 48 | — | 93.15 | 91.58 | — | 92.37 (1.11) |
| 72 | — | 91.25 | 89.25 | — | 90.30 (1.48) |

TABLE 14

Clinical Product Experience: SDF-1/VEGF/CXCR-4 mediated CD34+ cell migration (% migrating CD34+ cells as a function of time after MMH)

| Time (h) after MMH | Migrating CD34+ cells (%) | | | | Average (SD) |
|---|---|---|---|---|---|
| | A | B | C | D | |
| 12 (X) | 14.31 | 13.08 | 9.74 | 31.73 | 17.97 (11.34) |
| % Remaining | 100.0 | 100.0 | 100.0 | 100.0 | 100.0 (0) |
| 33 (Y) | — | 6.17 | — | — | 6.17 |
| *% Remaining | — | 47.17 | — | — | 47.17 |
| 48 (Y) | — | 4.88 | 8.21 | — | 6.55 (2.35) |
| *% Remaining | — | 37.30 | 84.29 | — | 60.79 (23.49) |
| 72 (Y) | — | 3.7 | 6.6 | — | 5.15 (2.05) |
| *% Remaining | — | 28.29 | 21.19 | — | 24.74 (3.55) |

*= (Y ÷ X) × 100%

All remaining ratios were calculated as in Table 8 above.

TABLE 15

Clinical Product Experience: # of CPU per 100 viable CD34+ cells plated as a function of time after MMH

| Time (h) after MMH | # of CFU per 100 viable CD34+ cells plated | | | | Average (SD) |
|---|---|---|---|---|---|
| | A | B | C | D | |
| 12. | 98.14 | 33.30 | 24.00 | 22.50 | 44.49 (36.09) |
| 33 | — | 16.50 | — | — | 16.5 |
| 48 | — | 19.56 | 20.50 | — | 20.03 (0.66) |
| 72 | — | 20.45 | 21.19 | — | 20.82 (1.10) |

Based on these data, extension of the in-dating to 24 hours (from 12-hours) and the out-dating to 72 hours (from 48 hours) for the CD34+ cell clinical product of the present invention is justified.

FIG. 1 indicates the equivalence of the functional viability of the chemotactic hematopoietic cell product of the present invention at 72 hours to the same indices evaluated at 48 hours.

Study 3: Catheter Safety.

The viability and potential efficacy of the chemotactic hematopoietic stem cell product of the present invention comprising potent CD34+ cells depends on the cells maintaining their potency as they pass through a catheter. The catheter used in the methods of the present invention has an internal diameter of at least 0.36 mm. Any type of catheter having an internal diameter of at least 0.36 mm may be effective in delivering the pharmaceutical compositions of the present invention.

In one embodiment, the catheter is a balloon catheter. Balloon catheter safety studies were conducted to determine whether high cell concentrations and repeated perfusions adversely affect cell viability, cell recovery or catheter integrity. Non-mobilized peripheral blood progenitors were used in order to obtain an adequate number of cells to perform the analysis. Catheters were assessed for infusion of the cell product of the present invention comprising selected CD34+ cells through the IRA. None of the 0.36 mm internal diameter catheters tested adversely affected CD34+ selected cell viability, growth in culture, or mobility in CXCR-4 assays.

TABLE 16

Viability of CD34+ cells before and after infusions through the catheters.

| Catheter | Condition | Viability (%) | | | | |
|---|---|---|---|---|---|---|
| | | 1 | 2 | 3 | 4 | 5 |
| — | Pre-infusion | | | 81.45 | | |
| Raptor | After 1st infusion | 84.29 | 70.94 | 87.89 | 88.02 | 84.68 |
| | After 2nd infusion | 83.00 | 87.44 | 86.39 | 79.91 | 83.18 |
| Sprinter | After 1st infusion | 93.39 | 91.09 | 84.13 | 88.28 | 81.68 |
| | After 2nd infusion | 91.89 | 91.08 | 84.88 | 77.65 | 77.73 |
| Voyager | After 1st infusion | 94.21 | 86.21 | 83.08 | 77.53 | 69.68 |
| | After 2nd infusion | 88.03 | 84.71 | 79.27 | 78.11 | 76.80 |
| Maverick | After 1st infusion | 90.00 | 89.76 | 90.79 | 85.49 | 81.31 |
| | After 2nd infusion | 90.94 | 87.38 | 81.98 | 80.09 | 85.47 |

As shown in Table 16, in all catheters tested, average $CD34^+$ cell viability was at or above 70% following passage through the catheters.

To demonstrate that infusion of the CD34+ cell product does not pose any safety breach of the catheter used and that a significant percentage of cell product does not adhere to the interior walls of the catheter, catheters were challenged with repeat infusions of a CD34+ cell product having a considerably higher cell concentration than that used clinically. Four brands of catheters (Sprinter, Voyager, Maverick and Raptor) were evaluated using 5 catheters of each type. Non-mobilized apheresis products were used in order to obtain an adequate number of cells to perform the analysis. A cell concentration greater than three times that planned as treatment doses for the trial, i.e., $160 \times 10^6$ nucleated cells containing CD34+ cells in 10 ml of infusion solution, was passed twice through each catheter. The average CD34+ cell recovery was 100.59% (based on a range of 76.99% to 228.70%) following passage through the catheters.

All twenty catheters were tested for integrity using a methylene blue dye leak test after two perfusions with the nucleated cells. There was no evidence of leakage and the contact points and catheter tips were normal upon inspection.

As shown in Table 17a and 17b, the effect on the cells of their perfusion through a catheter appears to be independent of catheter model and make among those catheters tested and was independent of the amount of time the cells were stored either prior to processing and/or after CD34+ cell selection and prior to perfusion, resulting in a final formulation containing an average recovery of 96.0% (range 80.8%-102.2%) of the CD34+ cells (Table 17b) and 86.36% of the CD45+ cells perfused through the catheter. Further, the average viability of the cells was 96.5% (range 92.5%-98.6%, N=16); the cells maintained both CXCR-4 migratory capacity (data not shown) and their ability to form hematopoietic colonies in methylcellulose (average 25.8 CFU/100 cells seeded (range 21.0%-30.5%)

TABLE 17a

CD45 cell recovery and viability after being infused through the catheters.

| Catheter | Condition | 1 | | 2 | | 3 | | 4 | | 5 | | Average | |
|---|---|---|---|---|---|---|---|---|---|---|---|---|---|
| | | Recovery | R'd viab | Recovery | R'd viab | Recovery | R'd viab | Recovery | R'd viab | Recovery | R'd viab | Recovery | R'd viab |
| Raptor | After 1st infusion | 69.68% | −1.35% | 78.67% | 2.08% | 72.14% | −4.55% | 80.54% | 1.83% | 73.21% | −2.13% | 74.85% (30.83%) | −0.82% (2.53%) |
| | After 2nd infusion | 97.91% | −8.55% | 81.84% | −4.76% | 142.98% | 3.28% | 107.82% | −8.48% | 94.08% | 0.08% | 104.93% (47.60%) | −3.69% (4.94%) |
| Sprinter | After 1st infusion | 76.74% | −0.60% | 68.56% | 4.01% | 72.63% | 5.29% | 73.61% | 6.06% | 66.83% | 8.31% | 71.67% (29.48%) | 4.61% (3.51%) |
| | After 2nd infusion | 78.82% | 2.86% | 85.40% | 0.98% | 90.29% | −1.02% | 82.22% | 6.50% | 91.61% | 0.00% | 85.67% (35.30%) | 1.86% (2.76%) |
| Voyager | After 1st infusion | 87.38% | 1.58% | 83.93% | −0.36% | 103.58% | 0.93% | 95.82% | 4.52% | 131.55% | −4.39% | 100.45 (44.39%) | 0.46% (2.91%) |
| | After 2nd infusion | 82.70% | 7.01% | 69.34% | 15.90% | 69.54% | 10.40% | 89.04% | 0.27% | 69.03% | 7.50% | 75.93% (32.11%) | 8.22% (6.09%) |
| Maverick | After 1st infusion | 73.97% | 1.58% | 87.01% | 0.42% | 78.31% | 0.69% | 75.53% | 2.61% | 77.22% | 2.95% | 78.41% (32.33%) | 1.65% (1.21%) |
| | After $2^{ndX}$ infusion | 152.35% | −5.06% | 73.44% | 2.78% | 80.85% | −3.92% | 97.10% | −2.97% | 91.11% | −2.07% | 98.97% (49.11%) | −2.25% (2.85%) |
| | | | | | | | | | | | Average of all catheters: | 86.36% | 1.26% |

[a] Recovery of CD45+ cells = (# of CD45 cells after infusion ÷ # of CD45 before infusion) × 100%
[b] Reduction of CD45+ cell viability = [1 − (CD45+ cell viability % after infusion ÷ CD45+ cell viability % before infusion)] × 100%

TABLE 17b

CD34 cell recovery and viability after being infused through the catheters.

| Catheter used | Condition | 1 Recovery[a] | R'd viab[b] | 2 Recovery | R'd viab | 3 Recovery | R'd viab |
|---|---|---|---|---|---|---|---|
| Raptor | After 1st infusion | 116.49% | −3.48% | 121.62% | 12.91% | 110.89% | −7.91% |
|  | After 2nd infusion | 91.66% | 1.53% | 85.18% | −23.26% | 122.47% | 1.71% |
| Sprinter | After 1st infusion | 89.19% | −14.66% | 83.34% | −11.83% | 102.72% | −3.29% |
|  | After 2nd infusion | 103.52% | 1.61% | 99.82% | 0.01% | 82.11% | −0.89% |
| Voyager | After 1st infusion | 81.02% | −15.67% | 96.08% | −5.84% | 90.16% | −2.00% |
|  | After 2nd infusion | 106.48% | 6.56% | 81.66% | 1.74% | 95.04% | 4.58% |
| Maverick | After 1st infusion | 76.99% | −10.50% | 101.79% | −10.21% | 98.62% | −11.46% |
|  | After 2nd infusion | 228.70% | −1.05% | 88.66% | 2.65% | 103.35% | 9.70% |

| Catheter used | Condition | 4 Recovery | R'd viab | 5 Recovery | R'd viab | Average Recovery (SD) | R'd viab (SD) |
|---|---|---|---|---|---|---|---|
| Raptor | After 1st infusion | 97.55% | −8.06% | 96.14% | −3.97% | 108.54% (45.46%) | −2.10% (7.79%) |
|  | After 2nd infusion | 111.33% | 9.21% | 98.96% | 1.78% | 101.92% (43.73%) | −1.81% (11.14%) |
| Sprinter | After 1st infusion | 84.57% | −8.39% | 88.65% | −0.28% | 89.69% (37.26%) | −7.69% (6.16%) |
|  | After 2nd infusion | 114.87% | 12.05% | 100.45% | 4.84% | 100.15% (42.22%) | 3.52% (4.90%) |
| Voyager | After 1st infusion | 82.73% | 4.82% | 89.32% | 14.46% | 87.86% (36.28%) | −0.85% (10.13%) |
|  | After 2nd infusion | 94.81% | −0.75% | 91.01% | −10.23% | 93.80% (39.12%) | 0.38% (5.86%) |
| Maverick | After 1st infusion | 112.58% | −4.96% | 96.05% | 0.18% | 97.21% (41.34%) | −7.39% (5.34%) |
|  | After 2nd infusion | 89.35% | 6.31% | 117.63% | −5.12% | 125.54% (73.48%) | 2.50% (5.33%) |
|  | Average of all catheters: |  |  |  |  | 100.59% | −1.68% |

[a] Recovery of CD34+ cells = (# of CD34 cells after infusion ÷ # of CD34 before infusion) × 100%
[b] Reduction of CD34+ cell viability = [1 − (CD34+ cell viability % after infusion ÷ CD34+ cell viability % before infusion)] × 100%

Collectively these experiments demonstrate that the serial passage of a chemotactic hematopoietic stem cell product comprising CD34+ cells through a cardiac catheter with an internal diameter of at least about 0.36 mm does not adversely affect either catheter integrity or CD34+ cell potency, i.e., CD34+ cell viability, CFU colony growth, or CD34+ CXCR+ mediated migratory capacity/mobility.

Study 4: Compatibility of the Cell Product with the Catheters

To further test the compatibility of the chemotactic hematopoietic stem cell product comprising CD34+ cells with each of the catheters that may be used for delivery of the cell product in the study, cell products were tested after multiple passages through each catheter type to evaluate the effects of extreme conditions of stress that would be greater than those expected during the treatment protocol.

At 48 hours post-MMH harvest, the chemotactic hematopoietic stem cell product comprising a range of about 5.73× $10^6$ CD34+ cells to about 21.10×$10^6$ CD34+ cells (i.e., dosages reflective of the treatment cohort) obtained from individual donors was infused sequentially through three catheters of the same brand, one type of catheter for each donor (Sprinter, Voyager or Maverick), and the cell product assessed for CD34+ cell recovery, colony formation and viability.

TABLE 18

CD34+ cell recovery and sterility after sequential infusions through the catheters.

| Condition | Parameter | Catheter used Sprinter | Voyager | Maverick |
|---|---|---|---|---|
| Pre-infusion | CD34+ cell yield | 9.72 × $10^6$ | 2.11 × $10^7$ | 5.73 × $10^6$ |
| After 1st catheter | CD34+ cell recovery | 111% | 103% | 99% |
| After 2nd catheter | CD34+ cell recovery | 94% | 104% | 97% |
| After 3rd catheter | CD34+ cell recovery | 99% | 99% | 106% |
|  | Sterility (aerobic and anaerobic microbes) | Negative | Negative | Negative |

As shown in Table 18, viable, colony forming cells were recovered in all experiments for all three catheters tested (cell recovery 99%, 99% and 106%).

As shown in Table 19, the average viability of the CD34+ cells after passing through the third catheter was 94.000% (based on a range of 93.55%-94.40%) versus 96.01% (based on range of 94.18%-97.93%) of the pre-infusion cell product.

TABLE 19

CD34+ cell viability after sequential
infusions through the catheters.

| | CD34+ cell viability | | | |
|---|---|---|---|---|
| Condition | Sprinter | Voyager | Maverick | Average |
| Pre-infusion | 94.18% | 95.91% | 97.93% | 96.01% |
| After 1st catheter | 94.73% | 96.31% | 95.45% | 95.50% |
| After 2$^{nd}$ Catheter | 95.34% | 95.72% | 95.01% | 95.36% |
| After 3rd catheter | 93.55% | 94.40% | 94.04% | 94.00% |

As shown in Table 20, colony forming unit (CFU) growth derived from the CD34+ cells after passing through the third catheter was 95.27% (based on a range of 43.47%-163.64%) of the infusion product (i.e., the infused chemotactic hematopoietic stem cell product comprising CD34+ cells).

TABLE 20

CFU growth of CD34+ cells after sequential
infusions through the catheters.

| | CFU per 100 CD34+ cells cultured | | |
|---|---|---|---|
| Condition | Sprinter | Voyager | Maverick |
| Pre-infusion | 30.5 | 11.5 | 11.0 |
| After 1st catheter | 22.0 | 14.0 | 22.0 |
| After 2nd catheter | 20.5 | 4.0 | 19.0 |
| After 3rd catheter | 24.0 | 5.0 | 18.0 |
| Recovery from the pre-infused product after the 3rd catheter | 78.69% | 43.47% | 163.64% |
| Average recovery | | 95.27% | |

To determine the effect of catheter perfusion on CD34+ cell mobility and ability to grow in culture, a series of experiments were performed where MMH cells obtained from healthy donors were stored at 4° C. for 12 or 24 hours before initiation of Isolex processing. Isolated CD34+ cell product that had been stored for about 12 hours pre-Isolex processing then were stored at 4° C. until about 36 hours had elapsed from the end of processing, for a total of about 48 hours post MMH. At that time they were assessed for SDF-1/CXCR4 mobility and CFU growth pre and post perfusion through a 0.36 mm inner diameter (i.d.) cardiac balloon catheter. Similarly, cells that were stored pre-Isolex processing for 24 hours then were stored at 4° C. until 48 hours had elapsed from the end of Isolex processing, for a total of 72 hours, and then assessed.

TABLE 21

12 inbound/48 outbound and 48 hour inbound/72 hour outbound
from MMH: SDF-1/CXCR4 mobility (% population of migrated
CD34+ cells) and CFU (per 100 viable CD34+ plated)
pre catheter perfusion ("PRE") and post catheter perfusion
("POST")

| Time (h) after MMH Inbound/ outbound | SDF-1/CXCR4 mobility (%) // # of CFU per 100 viable CD34+ cells plated | | | | |
|---|---|---|---|---|---|
| | A | B | C | D | E |
| 12/48 PRE | 2.7 // 14 | 8.8 // 15 | 15.8 // 16 | — | — |
| 12/48 POST | 3.4 // 15 | 18.9 // 13 | 17.6 // 8 | — | — |
| 24/72 PRE | — | — | — | 34 // 37 | 18.9 // 27.5 |
| 24/72 POST | — | — | — | 34 // 43 | 23.5 // 24 |

The results in Table 21 demonstrate that neither CD34+ CXCR-4-mediated cell mobility nor the cell's ability to grow in culture at any of the time points tested was affected adversely by perfusion through a catheter having an internal diameter of at least 0.36 mm.

The Stabilizing Effect of Serum

The following data confirm the importance of the stabilizing effect of serum to the migratory capability of the selected CD34+ cells.

As shown in Table 22, no CXCR-4 migratory activity was observed for all samples tested including the pre-catheter infusion samples when the composition comprising a chemotactic hematopoietic stem cell product was formulated without serum.

TABLE 22

Chemotaxis of CD34+ cells after sequential infusions
through the catheters in the absence of serum.

| | Migration (%) | | |
|---|---|---|---|
| Condition | Sprinter | Voyager | Maverick |
| Pre-infusion | 0.0 | 0.0 | 0.1 |
| After 1st catheter | 0.0 | 0.0 | 0.0 |
| After 2nd catheter | 0.0 | 0.0 | 0.1 |
| After 3rd catheter | 0.0 | 0.0 | 0.0 |

Figure 2:
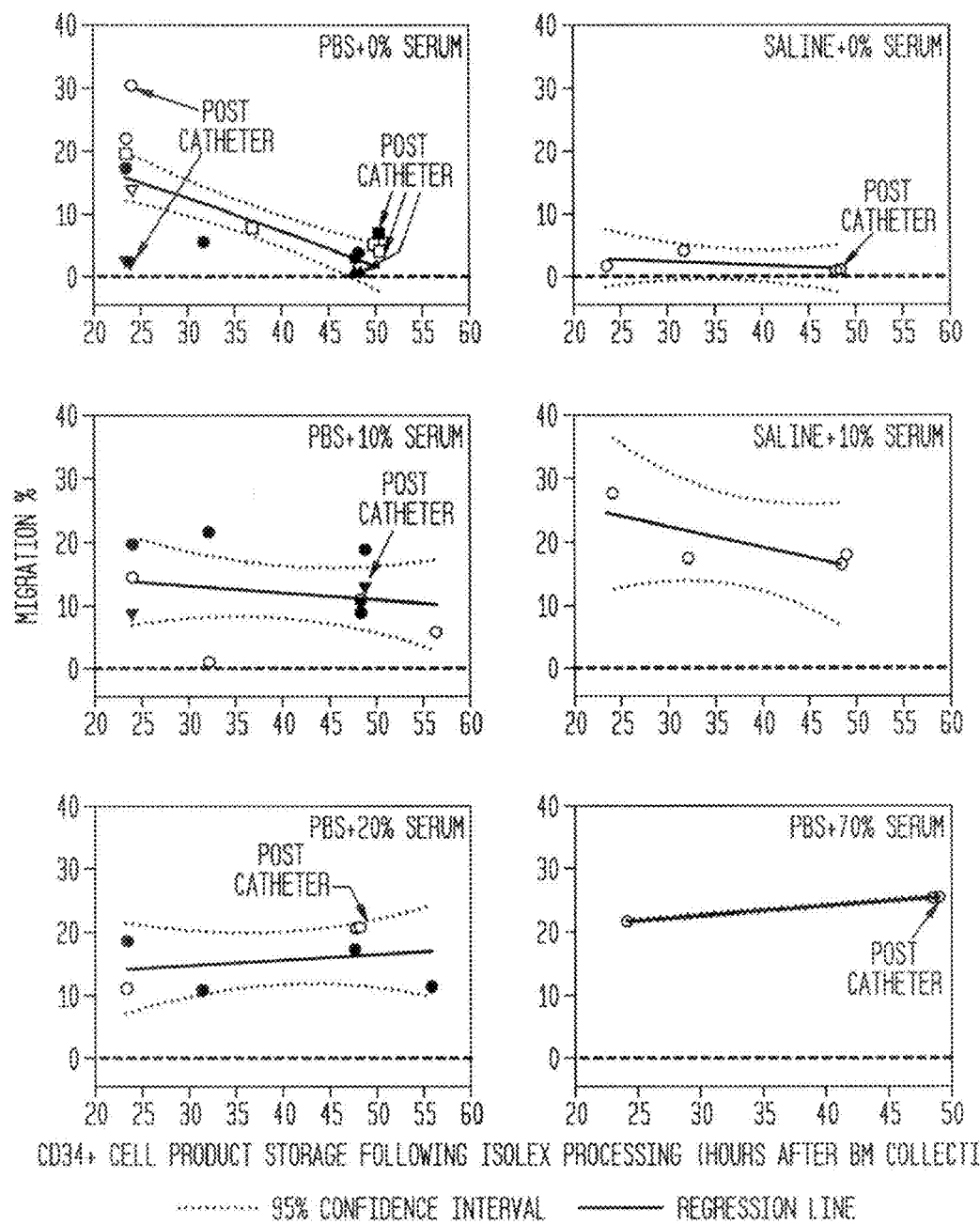
FIG. 2 shows the migratory efficiency of the formulated chemotactic hematopoietic stem cell product comprising CD34+ cells of the present invention.
Figure 3:
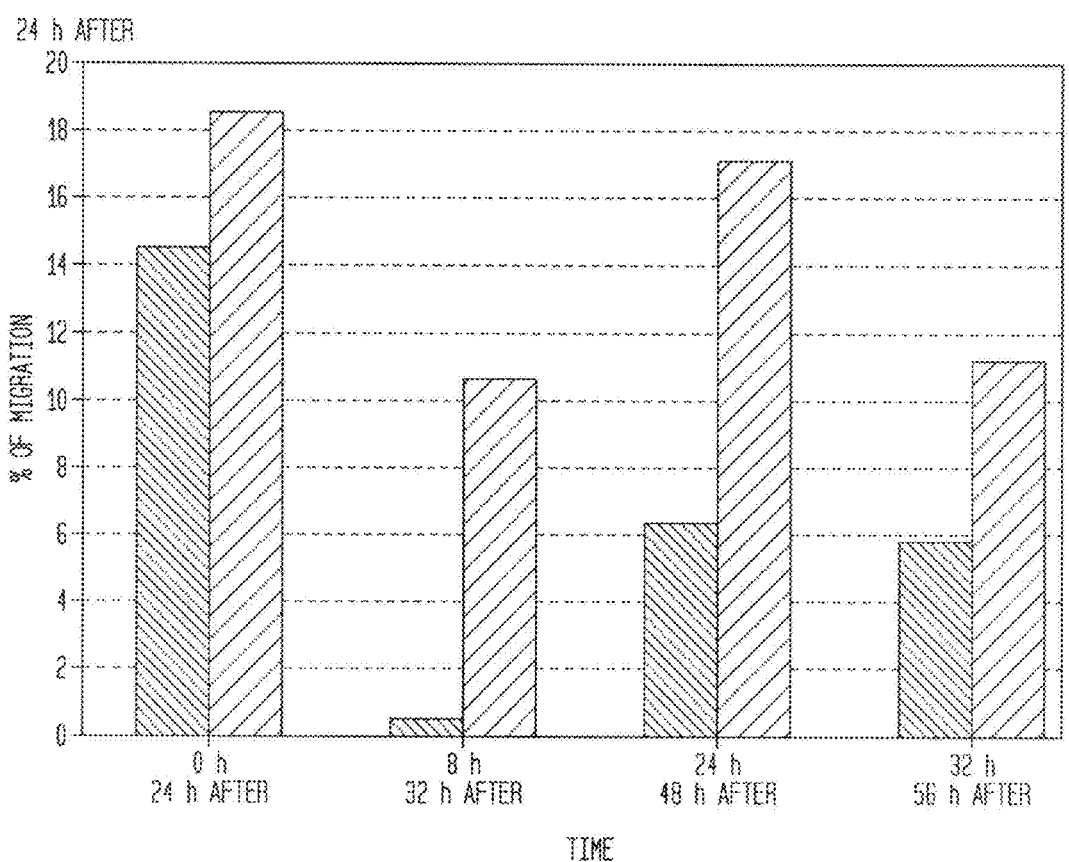
FIG. 3 shows the improved stability of CD34+ cells formulated in human serum.

FIGS. 2 and 3 further illustrate that Isolex selected CD34+ cells retain their migratory capacity longer when formulated in the presence of human serum. Following Isolex processing, the bone marrow derived hematopoietic stem cell product comprising selected CD34+ cells was formulated either in (1) phosphate buffered saline (Dulbecco's phosphate buffered saline, Ca++, Mg++Free (Baxter Cat. No. EDR9865) ("PBS") containing 1% human serum albumin, 25 U/ml of heparin sodium and various concentrations (about 0%, about 10%, about 20%, or about 70%) of autologous serum; or (2) normal saline (0.9%) containing 1% human serum albumin, 25 U/ml of heparin sodium and (about 0% or about 10%) autologous serum. SDF-1/CXCR-4 mediated CD34+ cell migratory capacity was evaluated at different times during final product storage (at 2° C.-8° C.) and after passing the cells through the catheter at the same rate and duration as anticipated by the clinical protocol. None of these formulations affected CD34+ cell viability or the recovery of CD34+ cells after they had been passed through the catheter.

Regardless of whether the chemotactic hematopoietic cell products comprising selected CD34+ cells was (i) formulated either in PBS-serum or in saline-serum and (ii) either passed through the catheter immediately or passed through the catheter after a prolonged stability testing storage interval at about 4° C. to about 8° C., they maintained an average of 96.6% viability (range 92.5%-98.6%) and an average CXCR-4-mediated migratory capacity of 11.4% (range 2.4%-30.6%), representing a total time from harvest to mobility analysis of up to 48 hours.

As shown in FIG. 2 panel (a), cells formulated in PBS alone at about 25 hours retained about 10% of their CXCR-4 migratory capacity, which dropped off to near 0 at about 48 hours. As shown in panel (b), cells formulated in normal saline alone retained little, if any, of their migratory capacity. As shown in panels (c) and (d), cells formulated with PBS containing at least about 10% serum retained about 10-15% of their migratory capacity for up to about 55 hours (c), while cells formulated with saline and at least about 10% serum retained about 20% of their migratory capacity for up to about 50 hours. As shown in panels (e) and (f), cells retained a higher migratory capacity for a longer duration in PBS supplemented with even higher concentrations of serum.

As shown in FIG. 3, the product of the present invention comprising selected CD34+ cells when formulated in 10% serum, retained 14.25%, <1%, 6%, and 5.8% of its CD34+ CXCR4-mediated migratory capacity about 24, about 32, about 48 and about 56 hours after harvest, respectively. FIG. 3 further shows that the product of the present invention comprising selected CD34+ cells when formulated in 20% serum retained 18.25%, 10.25%, 17% and 11% of its CD34+-CXCR4-mediated migratory capacity about 24, about 32, about 48 and about 56 hours after harvest, respectively. The term "stabilizing amount" as used herein therefore refers to the amount of serum that, when included in the formulation of the product of the present invention comprising selected CD34+ cells, enables these cells to retain their CXCR-4 mediated chemotactic activity and hematopoietic colony forming ability.

Study 5: Final Product Sterility Testing

Due to the limited yield of CD34+ cells obtained from a 300-ml MMH, final cell product sterility will be assessed using the supernatant removed from the final product formulation in order to preserve cell product for infusion. Supernatant samples are loaded into the syringes in a manner identical to that used to load the cell product into the syringes used for infusion (see supra). To demonstrate that such a sample will be representative of the final cell product formulation, we inoculated selected CD34+ cells in infusion solution prior to centrifugation of the final product with *C. sporogenes* (13 CFU/ml), *P. aeruginosa* (2 CFU/ml), *S. aureus* (18 CFU/ml), *A. niger* (17 CFU/ml), *C. albicans* (3 CFU/ml) and *B. subtilis* (17 CFU/ml) (See table 22). After centrifugation, the sterility of both cell pellet and non-cell supernatant fractions was assessed using USP aerobic and anaerobic testing.

TABLE 23

Bacteria and fungi used for the sterility study.

| Microbe | Total # of microbes/ml | Total CFU/ml | Expected CFU/ml of inoculated sample (21 ml) |
|---|---|---|---|
| C. sporogenes | 400 | 279 | 13 |
| P. aeruginosa | 400 | 36 | 2 |
| S. aureus | 400 | 371 | 18 |
| A. niger | 400 | 356 | 17 |
| C. albicans | 400 | 62 | 3 |
| B. subtilis | 400 | 349 | 17 |

Each source microorganism vial prepared by Microbiological Environments contained 400 microbes per ml, but the numbers of CFU derived from each species are varied.

As shown in Table 24, both the cell pellet fraction and suspension fractions from all tested samples showed outgrowth of the inoculated microorganisms, while un-inoculated controls showed no growth. Further, no apparent differential growth rate was observed between testing of cell pellet fractions and the suspension fractions for all microorganisms tested. Samples taken before each step of the processing procedure and following the final perfusion through the catheters all tested negative for microbial contamination.

TABLE 24

14-day sterility testing of nucleated cell (NC) samples inoculated with specific species of microorganism (400 microbes in 21-ml NC sample).

| Sample with microbe Inoculated | Medium type | Sample fraction | Test 1 | Test 2 | Test 3 |
|---|---|---|---|---|---|
| C. sporogenes | FTM[a] | Cell pellet | Positive | Positive | Positive |
| | | Suspension | Positive | Positive | Positive |
| S. aureus | FTM | Cell pellet | Positive | Positive | Positive |
| | | Suspension | Positive | Positive | Positive |
| P. aeruginosa | FTM | Cell pellet | Positive | Positive | Positive |
| | | Suspension | Positive | Positive | Positive |
| A. niger | TSB[b] | Cell pellet | Positive | Positive | Positive |
| | | Suspension | Positive | Positive | Positive |
| C. albicans | TSB | Cell pellet | Positive | Positive | Positive |
| | | Suspension | Positive | Positive | Positive |
| B. subtilis | TSB | Cell pellet | Positive | Positive | Positive |
| | | Suspension | Positive | Positive | Positive |
| Positive control: C. sporogenes | FTM | Cell | Positive | | |
| Positive control: S. aureus | FTM | suspension | Positive | | |
| Positive control: P. aeruginosa | FTM | | Positive | | |
| Positive control: A. niger | TSB | | Positive | | |
| Positive control: C. albicans | TSB | | Positive | | |
| Positive control: B. subtilis | TSB | | Positive | | |
| Negative control: No microbes | FTM | Cell | Negative | | |
| Negative control: No microbes | TSB | suspension | Negative | | |

[a]Fluid thioglycollate medium
[b]Tryptic soy broth

Preclinical Study Summary

Collectively, these preclinical data indicate that the manufacturing and testing procedures described are capable of generating adequate numbers of viable cells with adequate stability to withstand shipment and perfusion through the catheter in a manner that should pose no additional safety concerns to the subject other than those associated with the routine use of fluid infusion through the balloon catheter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A sterile pharmaceutical composition for repair or a vascular injury caused by vascular insufficiency comprising:
   (a) a vascular injury-repairing amount of a sterile chemotactic hematopoietic stem cell product, wherein the vascular injury-repairing amount is effective to repair a vascular injury caused by vascular insufficiency, the chemotactic hematopoietic stem cell product comprising a nonexpanded, isolated population of autologous mononuclear cells enriched for CD34+cells, which further contains a subpopulation of potent CD34+cells that express CXCR-4 and that have CXCR-4-mediated chemotactic activity, and
   (b) a stabilizing amount of serum, wherein the stabilizing amount of serum is greater than 20% (v/v),
   wherein the pharmaceutical composition is further characterized as having the following properties for at least 24 hours following acquisition of the chemotactic hematopoietic stem cell product when tested in vitro after passage through a catheter:
   (i) at least 70% of the cells are CD34+cells,
   (ii) contains a subpopulation of potent CD34+/CXCR-4+ cells that have CXCR-4-mediated chemotactic activity;
   (iii) is at least about 70% viable; and
   (iv) is able to form hematopoietic colonies in vitro.

2. The sterile pharmaceutical composition according to claim 1, wherein the nonexpanded, isolated population of autologous mononuclear cells containing CD34+cells, which further contains a subpopulation of potent CD34+cells that express CXCR-4 and that have CXCR-4-mediated chemotactic activity is purified from cellular components of a bone marrow aspirate.

3. The sterile pharmaceutical composition according to claim 1, wherein the pharmaceutical composition is further characterized as having the following properties for at least 48 hours following acquisition of the chemotactic hematopoietic stem cell product when tested in vitro after passage through a catheter:
   (a) is capable of forming hematopoietic colonies in vitro; and
   (b) retains at least 2% of the chemotactic activity of the CXCR-4-mediated chemotactic activity of the subpopulation of potent CD34+/CXCR-4+cells that have CXCR-4-mediated chemotactic activity.

4. The sterile pharmaceutical composition according to claim 1, wherein the pharmaceutical composition is further characterized as having the following properties for at least 72 hours following acquisition of the chemotactic hematopoietic stem cell product when tested in vitro after passage through a catheter:
   (a) is capable of forming hematopoietic colonies in vitro; and
   (b) retains at least 2% of the chemotactic activity of the CXCR-4-mediated chemotactic activity of the subpopulation of potent CD34+/CXCR-4+cells that have CXCR-4-mediated chemotactic activity.

5. The sterile pharmaceutical composition of claim 1, wherein the sterile pharmaceutical composition retains at least 2% of the chemotactic activity-of the CXCR-4-mediated chemotactic activity of the subpopulation of potent CD34+/CXCR-4+cells that have CXCR-4-mediated chemotactic activity for at least 24 hours following acquisition of the chemotactic hematopoietic stem cell product when tested in vitro after passage through a catheter.

6. The sterile pharmaceutical composition according to claim 1, wherein the composition is formulated for parenteral administration into a coronary blood vessel.

7. The sterile pharmaceutical composition according to claim 1, wherein the catheter is a flow control catheter.

8. The sterile pharmaceutical composition according to claim 1, wherein the catheter is a balloon catheter.

9. The sterile pharmaceutical composition according to claim 1, wherein the catheter has an internal diameter of at least about 0.36 mm.

10. The sterile pharmaceutical composition according to claim 1 wherein the composition is formulated for parenteral administration into myocardium.

11. The sterile pharmaceutical composition according to claim 1, wherein the pharmaceutical composition further includes at least one compatible active agent.

12. The sterile pharmaceutical composition according to claim 1, wherein sterility of the chemotactic hematopoietic cell product is confirmed by a method comprising the steps:
   (a) centrifuging the chemotactic hematopoietic cell product to form (i) a separated cell product comprising a pellet comprising the -isolated population of mononuclear cells enriched for CD34+cells and (ii) a supernatant;
   (b) removing the supernatant of the separated cell product without disturbing the cell pellet of the separated cell product.
   (c) analyzing the sterility of the supernatant of the separated cell product, thereby determining the sterility of the cell pellet of the separated cell product without depleting the chemotactic hematopoietic cell product.

13. The sterile pharmaceutical composition according to claim 1, wherein the nonexpanded, isolated population of autologous mononuclear cells containing CD34+cells, which further contains a subpopulation of potent CD34+cells that express CXCR-4 and that have CXCR-4-mediated chemotactic activity is purified from peripheral blood.

14. The sterile pharmaceutical composition according to claim 1, wherein the vascular insufficiency results from occlusion of a coronary artery.

15. The sterile pharmaceutical composition according to claim 14, wherein the vascular insufficiency resulting from occlusion of a coronary artery is a microvascular insufficiency.

16. The sterile pharmaceutical composition according to claim 14, wherein the vascular insufficiency resulting from occlusion of a coronary artery is an ischemia.

17. The sterile pharmaceutical composition according to claim 14, wherein the vascular insufficiency resulting from occlusion of a coronary artery is a transient vascular insufficiency.

18. The sterile pharmaceutical composition according to claim 14, wherein the vascular insufficiency resulting from occlusion of a coronary artery is a myocardial ischemia.

19. The sterile pharmaceutical composition according to claim 14, wherein the vascular insufficiency resulting from occlusion of a coronary artery produces a myocardial infarction.

20. The sterile pharmaceutical composition according to claim 1, wherein the vascular injury-repairing amount of the chemotactic hematopoietic stem cell product comprises at least $0.5 \times 10^6$ potent CD34+cells that express CXCR-4 and that have CXCR-4 mediated chemotactic activity.

21. The sterile pharmaceutical composition according to claim 1, wherein the CD34+/CXCR-4+cells of the sterile pharmaceutical composition migrate to and repair damage caused by the vascular insufficiency.

22. The sterile pharmaceutical composition according to claim 21, wherein migration of the CD34+/CXCR-4+cells of the sterile pharmaceutical composition is driven by chemotaxis.

23. The sterile pharmaceutical composition according to claim 22, wherein the chemotaxis is Mediated by at least one of SDF-1 and CXCR-4.

* * * * *